(12) United States Patent
Sterling et al.

(10) Patent No.: US 10,905,342 B2
(45) Date of Patent: Feb. 2, 2021

(54) METHOD AND SYSTEM FOR DETERMINING CARDIAC PERFORMANCE

(71) Applicant: Cardiac Profiles, Inc., Franklin, TN (US)

(72) Inventors: Bernhard B. Sterling, Danville, CA (US); Andrew R. Lawrence, Eagan, MN (US); Gregory I. Voss, Solana Beach, CA (US); James M. Perry, Nashville, TN (US); Rankin A. Clinton, III, Franklin, TN (US)

(73) Assignee: Cardiac Profiles, Inc., Franklin, TN (US)

( * ) Notice: Subject to any disclaimer, the term of this patent is extended or adjusted under 35 U.S.C. 154(b) by 0 days.

(21) Appl. No.: 14/323,828

(22) Filed: Jul. 3, 2014

(65) Prior Publication Data

US 2014/0323891 A1    Oct. 30, 2014

Related U.S. Application Data

(63) Continuation of application No. 12/459,570, filed on Jul. 2, 2009, now abandoned.

(60) Provisional application No. 61/133,876, filed on Jul. 2, 2008.

(51) Int. Cl.
*A61B 5/029* (2006.01)

(52) U.S. Cl.
CPC .................................. *A61B 5/029* (2013.01)

(58) Field of Classification Search
None
See application file for complete search history.

(56) References Cited

U.S. PATENT DOCUMENTS

| | | | |
|---|---|---|---|
| 5,265,615 A | 11/1993 | Frank et al. | |
| 5,390,679 A | 2/1995 | Martin | |
| 5,400,793 A | 3/1995 | Wesseling | |
| 5,535,753 A | 7/1996 | Petrucelli et al. | |
| 5,584,298 A | 12/1996 | Kabal | |
| 5,647,369 A | 7/1997 | Petrucelli et al. | |
| 5,758,652 A | 6/1998 | Nikolic | |
| 5,797,395 A | 8/1998 | Martin | |
| 5,836,884 A | 11/1998 | Chio | |
| 5,913,826 A | 6/1999 | Blank | |
| 2002/0058876 A1* | 5/2002 | Chen | A61B 5/021 600/485 |

(Continued)

OTHER PUBLICATIONS

G. V. R. K. Sharma, et al., "Evaluation of a Noninvasive System for Determining Left Ventricular Filling Pressure", Arch. Intern. Med., vol. 162, pp. 2084-2088, Oct. 14, 2002.

(Continued)

*Primary Examiner* — Michael R Bloch
(74) *Attorney, Agent, or Firm* — Steven R. Vosen

(57) ABSTRACT

Methods, associated algorithms, and systems for determining cardiac and/or cardiovascular performance from three measurements on a subject are presented, where two of the measurements are provided by plethysmographs and one measurement is provided by an electrocardiogram. The two plethysmographs are placed different distances from the subject's heart. Certain embodiments use the three measurements to calculate intermediate variables of a left ventricular ejection time and a pre-ejection period.

4 Claims, 10 Drawing Sheets

(56) References Cited

U.S. PATENT DOCUMENTS

| | | | |
|---|---|---|---|
| 2003/0120164 A1* | 6/2003 | Nielsen | A61B 5/02055 600/513 |
| 2003/0199770 A1* | 10/2003 | Chen | A61B 5/021 600/485 |
| 2005/0070774 A1* | 3/2005 | Addison | A61B 5/14551 600/323 |
| 2006/0212484 A1* | 9/2006 | Chaffin, Jr. | G06F 19/322 |
| 2006/0217615 A1* | 9/2006 | Huiku | A61B 5/08 600/484 |
| 2009/0099424 A1* | 4/2009 | O'Brien | A61B 5/02028 600/301 |
| 2010/0016731 A1* | 1/2010 | Eggers | A61B 5/0059 600/476 |

OTHER PUBLICATIONS

C. Frank Starmer, et al., "Evaluation of Several Methods for Computing Stroke Volume from Central Aortic Pressure", Circulation Research, vol. 33, pp. 139-148, (1973).

T. Tajimi, et al., "Evaluation of Pulse Contour Methods in Calculating Stroke Volume From Pulmonary Artery Pressure Curve (Comparison With Aortic Pressure Curve)", European Heart Journal, vol. 4, pp. 502-511 (1983).

Zacharoulis, et al., Measurement of stroke volume from pulmonary artery pressure record in man, Br Heart J. Jan. 1975;37(1):20-5.

\* cited by examiner

METHOD AND SYSTEM FOR DETERMINING CARDIAC PERFORMANCE

CROSS-REFERENCE TO RELATED APPLICATIONS

This application is a continuation of application Ser. No. 12/459,570, filed Jul. 2, 2009, which claims the benefit of U.S. Provisional Application No. 61/133,876, filed Jul. 2, 2008, the contents of which are hereby incorporated by reference in their entirety.

FIELD OF THE PRESENT INVENTION

The present invention relates generally to methods and systems for determining cardiac function. More particularly, the invention relates to a method for determining cardiac performance as a function of multiple cardiac parameters.

BACKGROUND OF THE INVENTION

A clinical and scientific goal for many years has been to accurately and non-invasively determine myocardial or cardiac output of a patient or subject. Indeed, there is a vast array of methods for determining cardiac output in the prior art. While each of the prior art methods can be employed to provide an estimate of cardiac output, as discussed in detail below, the accuracy of the estimated cardiac output is limited by virtue of various methodological constraints, including the limited number of cardiac hemodynamic variables (or cardiac performance determinants) employed in the methodology.

Cardiac output is typically expressed as heart rate (i.e. the number of heart beats per unit of time) multiplied by stroke volume (i.e. the amount of blood ejected in each beat). The seminal factor is, however, stroke volume.

As is well known in the art, stroke volume is determined by three seminal cardiac parameters or factors; pre-load, after load and contractility. Preload is generally defined as the myocardial muscle, i.e. sarcomere, length prior to contraction (see FIG. 1). A key determinant or indices of preload is ventricular end-diastolic volume or pressure.

Afterload is the load that the myocardium must bear to contract. Referring to FIG. 1, afterload generally reflects systemic vascular resistance or compliance.

Contractility is the intrinsic ability of the myocardial muscle to develop the necessary blood ejection force for a given muscle length. Contractility generally reflects the level of activation and the formation and cycling of the cross bridges between actin and myosin filaments.

As is also well known in the art, there are multiple determinants that affect each of the noted cardiac parameters and, hence, stroke volume. The determinants include ventricular geometric form, left ventricular stiffness, left ventricular end diastolic volume, venous return, right atrial pressure, central venous pressure, mean systemic pressure, venous compliance and total peripheral resistance.

The noted determinants are typically assessed via one or more physiological measurements, i.e. signals provided by selective physiological measuring or monitoring devices, such as a pulse oximeter, EKG and blood pressure cuff. The signals are then often employed to generate physiological relationships or waveforms, such as a plethysmographic waveform, arterial pressure waveform and right ventricular waveform. The waveforms are then analyzed to determine one or more of the noted cardiac function or performance determinants, which can be employed to estimate cardiac stroke volume and/or cardiac output.

By way of example, U.S. Pat. No. 5,400,793 describes a method of determining the stroke volume and cardiac output of the human heart from a pulse-type blood-stream pressure signal. U.S. Pat. No. 5,265,615 describes a method and apparatus for continuous measurement of cardiac output by analyzing the blood pressure signal. U.S. Pat. Nos. 5,535,753 and 5,647,369 describe apparatus and methods for non-invasively measuring cardiovascular system parameters involving sensing a time varying arterial pressure pulse waveform.

U.S. Pat. No. 5,584,298 describes a noninvasive method for calculating stroke volume and cardiac output of a human heart using computerized algorithms. U.S. Pat. No. 5,758,652 describes a system and method for measuring the heart condition of a patient by utilizing blood pressure signals. U.S. Pat. No. 5,836,884 describes a method for determining the cardiovascular condition of a patient by determining peripheral resistance and diastolic flow velocity of the patient.

U.S. Pat. Nos. 5,390,679 and 5,797,395 describe a cardiac output determining device and method which senses an arterial pressure waveform and compares the sensed waveform and compares the sensed waveform to a plurality of stored waveforms representative of known states. U.S. Pat. No. 5,913,826 describes an apparatus and method for assessing the cardiovascular status of a mammal by utilizing arterial pressure waveforms and systolic and diastolic pressures.

See also, Sharma, et al., Evaluation of a Noninvasive System for Determining Left Ventricular Filing Pressure, Arch. Intern. Med., vol. 162, pp 2084-2088 (2002); Starmer, et al., Evaluation of Several Methods for Computing Stroke Volume from Central Aortic Pressure, Circ. Res., vol. 33, pp. 139-148 (1973); Tajimi, et al., Evaluation of Pulse Contour Methods in Calculating Stroke Volume From Pulmonary Artery Pressure Curve (Comparison With Aortic Pressure Curve), Eur. Heart J., vol. 4, pp 502-511 (1983); Xu, et al., Prediction of Pulmonary Arterial Wedge Pressure From Arterial Pressure or Pulse Oximetry Plethysmographic Waveform, Chin. Med. J., vol. 115(9), pp. 1372-1375 (2002); and Zacharoulis, et al., Estimation of Stroke Volume From the Pulmonary Artery Pressure Record, Cardiovasc. Res., vol. 8, pp. 506-516 (1974).

There is a vast array of additional prior art disclosing methods for determining cardiac output via analysis of various physiological measurements and physiological waveforms developed therefrom. While each of the prior art methods can be employed to provide an estimate of cardiac output, the accuracy of the estimated cardiac output is typically limited by virtue of various methodological constraints; particularly, the limited number of cardiac function determinants (or hemodynamic variables) employed in the methodology.

It would thus be desirable to provide methods and systems for determining cardiac performance that employ multiple cardiac determinants that represent (or account for) the three seminal cardiac parameters or factors, i.e. preload, afterload and contractility.

It is therefore an object of the present invention to provide methods and systems for determining cardiac performance that overcome the drawbacks and disadvantages associated with prior art methods and systems for determining cardiac function.

It is another object of the invention to provide methods and systems for determining cardiac performance that employ multiple cardiac determinants that represent (or account for) the three seminal cardiac parameters or factors, i.e. preload, afterload and contractility.

It is another object of the invention to provide methods and systems for determining cardiac stroke volume and output that employ multiple cardiac determinants to enhance the accuracy of the derived cardiac stroke volume and output.

SUMMARY OF THE INVENTION

In accordance with the above objects and those that will be mentioned and will become apparent below, the present invention provides improved methods for determining stroke volume and, hence, cardiac output that substantially reduces or eliminates the disadvantages and drawbacks associated with conventional methods and associated algorithms for determining cardiac output. As discussed in detail below, a key feature and, hence, advantage of the invention is that the methods and associated algorithms disclosed herein employ multiple cardiac function determinants that represent (or account for) the three seminal cardiac parameters or factors, i.e. preload, afterload and contractility. The cardiac stroke volume and, hence, cardiac output determined therefrom is thus highly accurate and clinically useful.

According to one embodiment of the invention, the methods and associated algorithms for determining cardiac and/or cardiovascular performance (CP) are based on at least one cardiac function determinant that is associated with or at least in part, reflective of preload, contractility and afterload.

In one embodiment of the invention, cardiac performance is accordingly determined and, hence, represented by the following equation $$CP = f(CFD_x; CFD_y; CFD_z)$$

where: $CFD_x$ is a cardiac function determinant associated with preload; $CFD_y$ is a cardiac function determinant associated with contractility; $CFD_z$ is a cardiac function determinant associated with afterload; and $f(CFD_x; CFR_y; CFD_z)$ is an empirical relationship between $CFD_x$, $CFD_y$, and $CFD_z$.

In accordance with another embodiment of the invention, the methods and associated algorithms for determining cardiac performance are based on multiple cardiac function determinants associated with or at least in part, reflective of each cardiac parameter, i.e. preload, contractility and afterload.

In one embodiment of the invention, cardiac performance, i.e. cardiac stroke volume, is accordingly determined and, hence, represented by the following equation $$SV = f_{co}(CFD_{(c)x}; CFD_{(c)y}; CFD_{(c)z})$$

where: SV is a cardiac stroke volume; $CFD_{(c)x}$ is a combination of cardiac function determinants associated with preload; $CFD_{(c)y}$ is a combination of cardiac function determinants associated with contractility; $CFD_{(c)z}$ is a combination of cardiac function determinant associated with afterload; and $f_{co}$ is a combination of empirical relationships or mathematical functions that combine $CFD_{(c)x}$, $CFD_{(c)y}$, and $CFD_{(c)z}$.

Certain embodiments of the invention provide a method of determining cardiac stroke index of a subject. The method includes obtaining a first plethysmographic signal from a first plethysmograph located on a first position of the subject, where the first position is proximate the central circulation system of the subject; obtaining a second plethysmographic signal from a second plethysmograph located on a second position of the subject, where the second position is at a peripheral point on the body of the subject; and obtaining an electrocardiogram (ECG) signal from an ECG sensor on the subject. The method further includes determining a cardiac stroke index (SI) by combining the first plethysmographic signal, the second plethysmographic signal, and the ECG signal.

Certain other embodiments of the invention provide an apparatus for determining cardiac stroke index of a subject. The apparatus includes a first plethysmograph to produce a first plethysmographic signal from a first position of the subject, where the first position is proximate the central circulation system of the subject; a second plethysmograph to produce a second plethysmograph signal from a second position of the subject, where the second position is at a peripheral point on the body of the subject; an ECG sensor adapted to obtain an electrocardiogram (ECG) signal from on the subject. The apparatus further includes electronics to determine a cardiac stroke index (SI) by combining the first plethysmographic signal, the second plethysmographic signal, and the ECG signal.

These features together with the various ancillary provisions and features which will become apparent to those skilled in the art from the following detailed description, are attained by the method and apparatus of the present invention, preferred embodiments thereof being shown with reference to the accompanying drawings, by way of example only, wherein:

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
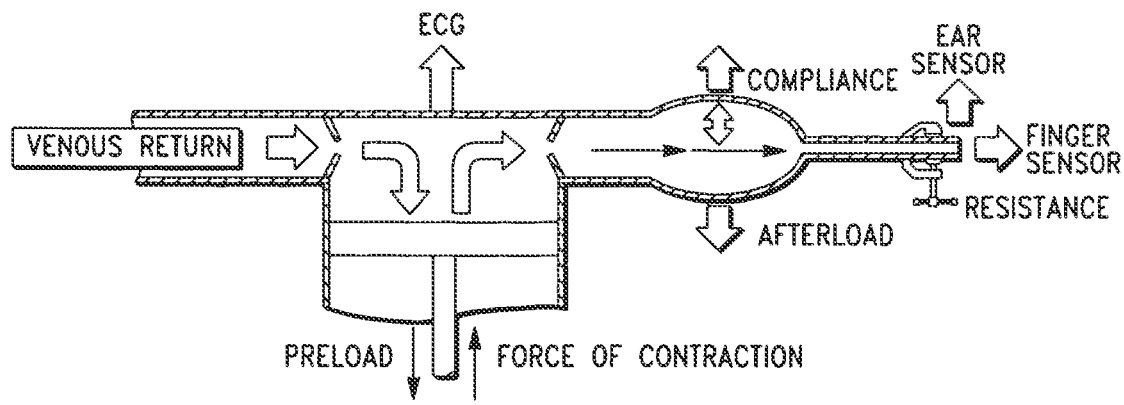
FIG. 1 is a schematic illustration of a heart and associated circulatory system, demonstrating the three seminal cardiac parameters, preload, contractility and afterload.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "an active agent" includes two or more such agents; reference to "a microprojection" includes two or more such microprojections and the like.

Definitions

The term "signal", as used herein, is meant to mean and include, without limitation, an analog electrical waveform or a digital representation thereof, which is collected or transmitted by a biological or physiological sensor, such as a photoplethysmographic tissue probe or electrocardiogram.

The term "cardiac cycle", as used herein, is meant to mean and include, without limitation, a sequence of contractions (systole), which results in an increase in pressure and expelling of blood into the arteries, and relaxations (diastole), which results in a decrease in pressure and the filling of the heart chambers from the veins.

The term "pre-ejection period", as used herein, is meant to mean and include the time from the onset of the QRS to the opening of the aortic valve during the cardiac cycle.

The term "stroke volume", as used herein, is meant to mean and include, without limitation, a measure of volume pumped per heartbeat, which is typically expressed as the volume of blood pumped from a ventricle of the heart in one beat.

The term "cardiac output", as used herein, is meant to mean and include, without limitation, a measure of the volume of blood pumped per unit of time, which is typically expressed as the volume of blood ejected from the left side of the heart in one minute, in units of liters per minute (l/min).

The term "cardiac index", as used herein, is meant to mean and include, without limitation, a cardio dynamic measure based on the cardiac output. Cardiac index is typically expressed as the amount of blood the left ventricle ejects into the systemic circulation in one minute, divided by the body surface area ("BSA"), i.e. the total surface area of the human body. The cardiac index typically has units of $(l/min)/m^2$.

The term "systolic blood pressure", as used herein, is meant to mean and include, without limitation, peak pressure in the arteries, which occurs near the end of the cardiac cycle when the ventricles are contracting.

The term "diastolic blood pressure", as used herein, is meant to mean and include, without limitation, minimum pressure in the arteries, which occurs near the beginning of the cardiac cycle when the ventricles are filled with blood.

The term "mean arterial pressure (MAP)", as used herein, is meant to mean and include, without limitation, the average pressure within an artery over a complete cycle of one heartbeat.

The term "blood volume", as used herein, is meant to mean and include, without limitation, the total amount of blood in the body.

The term "perfusion", as used herein, is meant to mean and include, without limitation, the passage of blood through one or more organs or tissues of the body.

The term "oxygen delivery", as used herein, is meant to mean and include, without limitation, the amount of oxygen carried by the blood and delivered to one or more organs or tissues of the body.

The term "oxygen extraction", as used herein, is meant to mean and include, without limitation, the amount of oxygen extracted from the blood by one or more organs or tissues.

The term "systemic vascular resistance", as used herein, is meant to mean and include, without limitation, an index of arteriolar constriction throughout the body.

The term "stenosis", as used herein, is meant to mean and include, without limitation, an abnormal narrowing in one or more areas of the vasculature of the body.

The term "cardiac performance", as used herein, is meant to mean a functional characteristic of the heart and associated cardiovascular system, including, without limitation, the aforementioned stroke volume, cardiac output and cardiac index. The term "cardiac performance" further means and includes, without limitation, systemic vascular resistance, perfusion, degree of stenosis, blood volume, mean arterial pressure, systolic blood pressure, diastolic blood pressure, hematocrit, oxygen extraction, and oxygen delivery.

The terms "patient" and "subject", as used herein, is meant to mean and include humans and animals.

The present invention provides improved methods for determining stroke volume and, hence, cardiac output, determined therefrom, that substantially reduces or eliminates the disadvantages and drawbacks associated with conventional methods and associated algorithms for determining cardiac output. As discussed in detail below, a key feature and, hence, advantage of the invention is that the methods and associated algorithms disclosed herein employ multiple cardiac determinants that represent (or account for) the three seminal cardiac parameters or factors, i.e. preload, afterload and contractility. The cardiac stroke volume and, hence, cardiac output determined therefrom as thus highly accurate and clinically useful.

Figure 2:
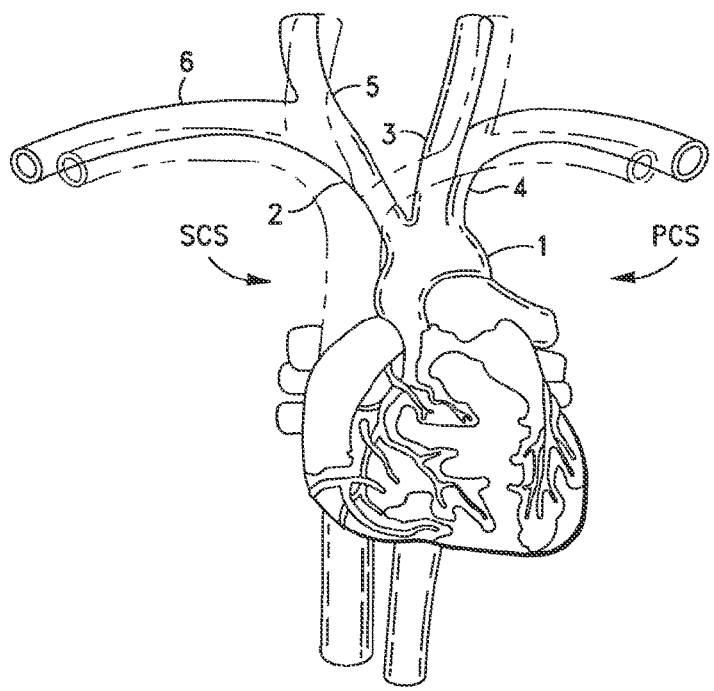
FIG. 2 is an illustration of a human heart, showing the pulmonary and systemic circulation sections.

Referring first to FIG. 2, there is shown an illustration of a human heart. As illustrated in FIG. 2, functionally, the heart is divided into two sides, i.e. right and left, or sections, i.e. pulmonary and systemic circulation sections. The right or pulmonary circulation section (designated "PCS") receives blood from the veins of the body and pumps it through the lungs. The left or systemic circulation section (designated "SCS") receives the blood from the lungs and pumps it to the body. The blood is then collected in the veins to be returned to the right side of the heart.

The arterial system begins at the aorta 1, to which the left ventricle of the heart pumps. The aorta 1 passes down (caudad) through the body, providing arterial branches to organs, and terminates as a bifurcation, i.e. creating the iliac arteries.

The first three branches of the aorta 1 are the brachiocephalic or innominate artery 2, the left (common) carotid artery 3, and the left subclavian artery 4. The brachiocephalic artery 2 branches into the right subclavian 5 and right (common) carotid arteries. These arteries provide the blood supply for the head and upper extremities.

The brachiocephalic or innominate artery 2 is the first branch of the aorta 1. The innominate artery 2, in turn, branches into the right subclavian 5 and right carotid arteries 6. In contrast, the left subclavian 4 and left carotid arteries 3 originate directly off the aortic arch. Thus, the subclavian 4 and carotid arteries 3, as well as their branches, have different paths from their counterparts on the opposite side of the body.

Figure 3:
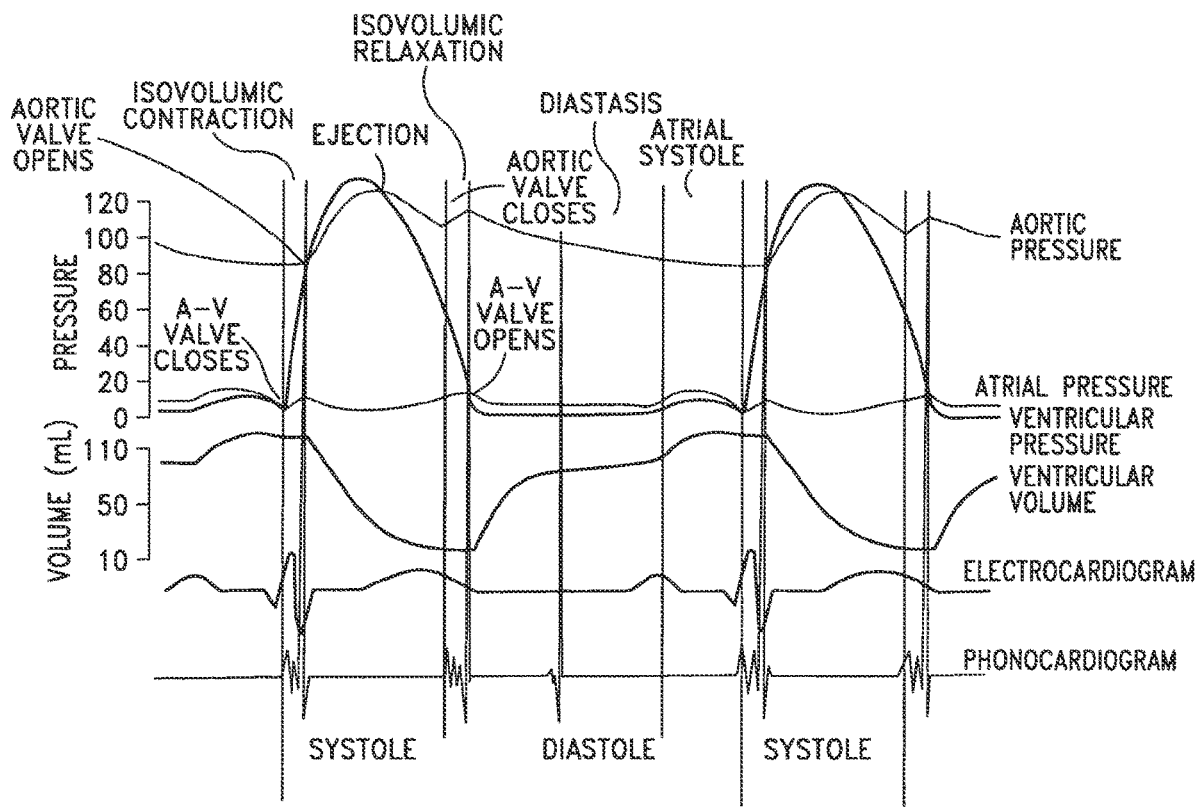
FIG. 3 is a graphical illustration of a cardiac cycle, showing cardiac events and changes in blood volume and pressure associated therewith.

Referring now to FIG. 3, there is shown a graphical illustration of a cardiac cycle (or heart beat), showing cardiac events and changes in blood volume and pressure associated therewith. As is well known in the art, a cardiac cycle is one of a sequence of contractions (systole), which, as illustrated in FIG. 3, results in an increase in pressure and expelling of blood into the arteries, and relaxations (diastole), which results in a decrease in pressure and the filling of the heart chambers from the veins.

The cardiac cycle is typically divided into distinct periods, i.e. diastole and systole, which are determined by electrical and mechanical events, i.e. diastolic and systolic events. The noted periods and events associated therewith are discussed in detail below.

Diastole is the period during which the filling of the ventricles occurs. Diastole is typically divided into four intervals: isovolumic relaxation, early diastolic filling, diastasis and atrial contraction.

At the end of systole, the semi-lunar valves shut and the ventricles relax, resulting in a fall in the intraventricular pressure. This is an active process, known as the period of isovolumic relaxation. Isovolumic relaxation ends when the pressure in the ventricles decreases to below that in the atria and the AV valves open (see FIG. 3).

At resting heart rates, the majority of the filling of the ventricles occurs during early diastolic filling. Early diastolic filling is often deemed a "passive" period, when the blood stored in the atrial "priming" chambers flows rapidly into the ventricles. Early diastolic filling ends when the elastic properties of the ventricle(s) or myocardial muscle (i.e. sarcomere) prevent further filling (the length of the stretched sarcomere defining "preload") and the pressure rises above that in the atria.

As illustrated in FIG. 3, diastasis is often the longest period in diastole. During diastasis, only a small amount of blood flows from the atria.

The second period of diastole, during which there is significant blood flow, is when the ventricles are actively filled by blood from atrial contraction. Atrial contraction includes a "pump-priming" action that increases the ventricular pressure immediately prior to systole.

Systole is the period during which the ventricles develop pressure to drive blood into the arteries. Systole is typically divided into three intervals: electromechanical delay, isovolumic contraction and the ejection period.

Electromechanical delay is the period of time taken for the electrical stimulus to result in activation of the ventricular muscle.

The period of isovolumic contraction is the period of time when the ventricles have begun to contract, but the volume of the chambers has not yet changed. It occurs immediately after the period of electromechanical delay, following electrical stimulation of the ventricles. During this period, intraventricular pressure increases until it is sufficient to open the semilunar valves and eject blood into the arteries (see FIG. 7).

As stated above, contractility is the index reflecting the intrinsic ability of the myocardial muscle to develop the necessary force to eject blood into the arteries.

The pre-ejection period ("PEP") typically includes both the electromechanical delay and isovolumic contraction.

The ejection period occurs when the semilunar valves have opened, and the ventricles eject the forward stroke volume into the systemic circulation, i.e. into the ascending aorta. There is a short period during which the velocity of blood flow accelerates to a peak, after which there is a gradual decline until the point at which the aortic pressure is sufficiently high to prevent further ejection of blood.

As is well recognized in the art, cardiac stroke volume, i.e. the volume of blood ejected from the heart per unit of time, is a seminal index of cardiac performance, which is dependent on (or determined by) three cardiac parameters or factors; preload, afterload and contractility.

As is also well known in the art, in cardiac physiology, preload is the pressure stretching the ventricle of the heart, after atrial contraction and subsequent passive filling of the left ventricle. Preload is theoretically most accurately described as the initial stretching of a single cardiac myocyte prior to contraction. Preload cannot, however, be measured in vivo and therefore other measurements are used to estimates preload. Estimations are, however, typically inaccurate. For example, in a chronically dilated ventricle new sarcomeres may have formed in the heart muscle allowing the relaxed ventricle to appear enlarged.

The term end-diastolic volume is better suited to the clinic, although not exactly equivalent to the laboratory term preload.

For purposes of this disclosure, preload is thus employed as a volume term.

Coordinated contraction of cardiac muscle cells in the heart propel blood from the atria and ventricles to the blood vessels of the circulatory system. For purposes of this disclosure, contractility is thus employed as the force term to describe the ejection of blood from a ventricle.

As is further well known in the art, in cardiac physiology, afterload is used to mean the tension produced by a chamber of the heart in order to contract. If the chamber is not mentioned, it is usually assumed to be the left ventricle. However, the strict definition of the term relates to the properties of a single cardiac myocyte. It is therefore only of direct relevance in the laboratory. In the clinic, the term end-systolic pressure is usually more appropriate, although not equivalent.

Afterload can also be described as the pressure that the chamber of the heart must generate in order to eject blood out of the chamber, and thus is a consequence of the aortic pressure, since the pressure in the ventricle must be greater than the systemic pressure in order to open the aortic valve. Everything else held equal, as afterload increases, cardiac output decreases.

For purposes of this disclosure, afterload is thus employed to indicate impedance and resistance to blood flow.

Figure 4:
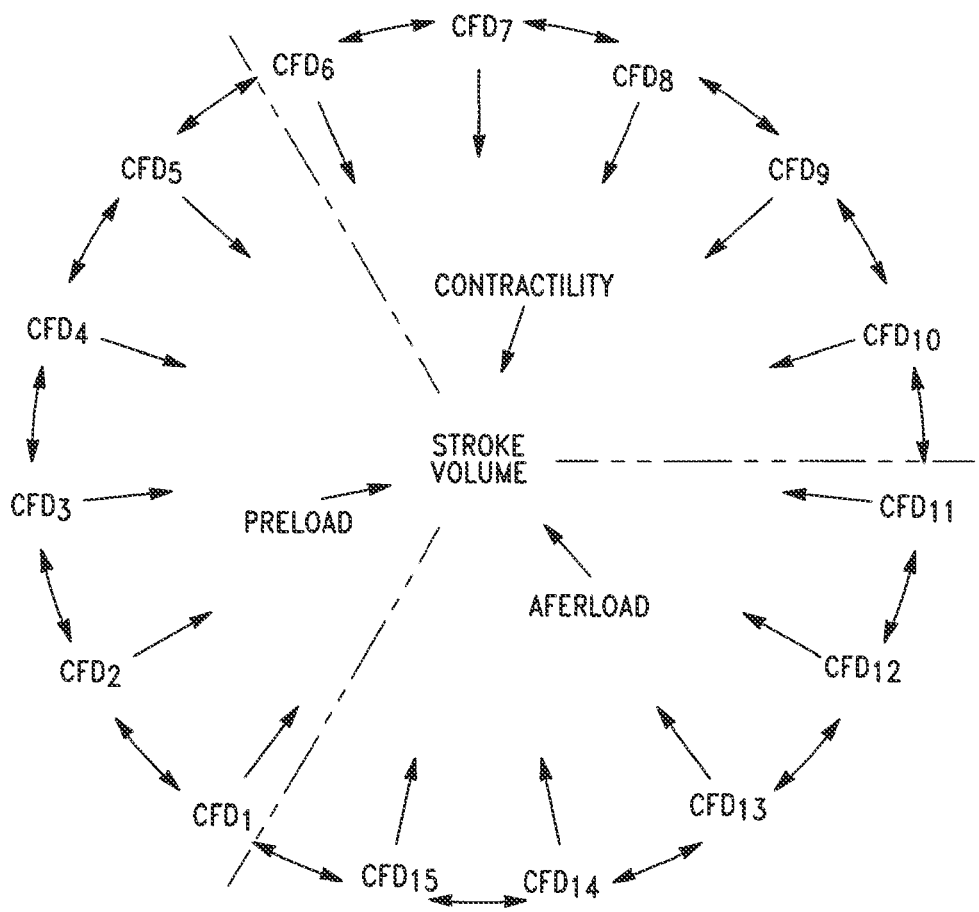
FIG. 4 is a schematic illustration of cardiac function determinants and the cardiac parameters associated therewith.

As illustrated in FIG. 4, there are multiple cardiac function determinants (denoted $CFD_{1-15}$) that can, and in many instances will, affect the noted cardiac parameters, i.e. preload, afterload and contractility, and, hence, cardiac stroke volume. The determinants include ventricular geometric form, left ventricular stiffness, left ventricular end diastolic volume, venous return, right atrial pressure, health condition of the myocardium, endogenous and exogenous effectors (drugs and agents), valvular conditions, viscosity of the blood, central venous pressure, mean systemic pressure, arterial and aortic compliance and total peripheral resistance.

Figure 5A:
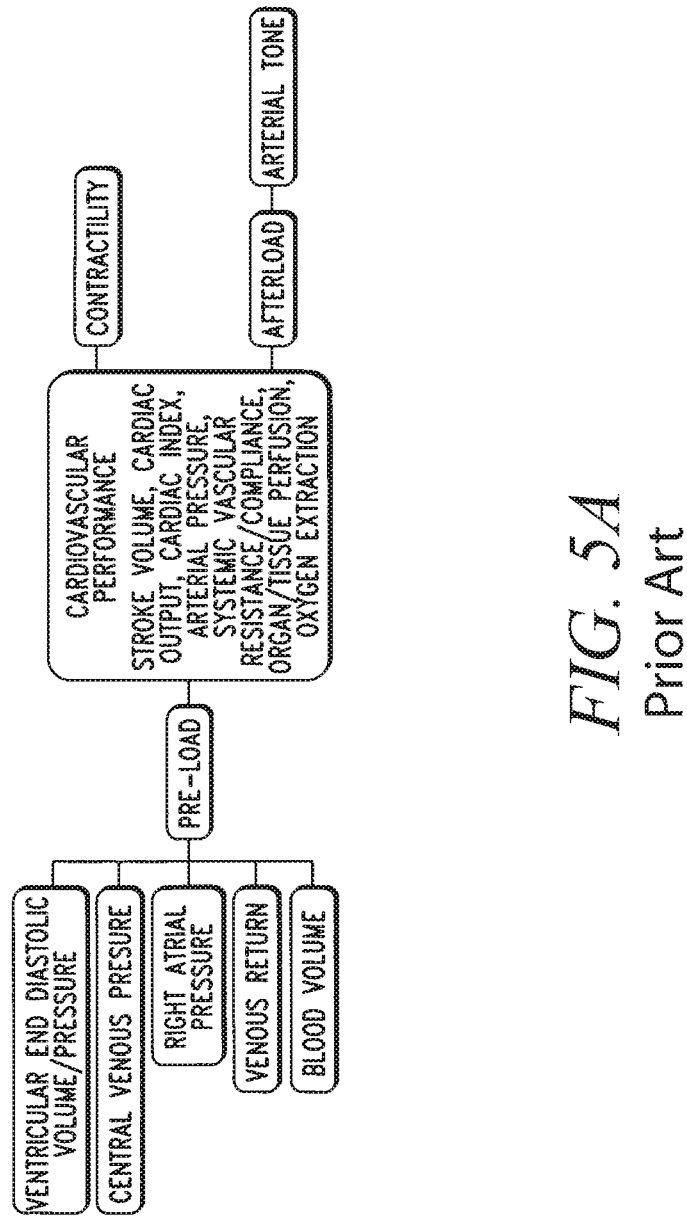
FIG. 5A is a schematic illustration of prior art cardiac function determinants and the cardiac parameters associated therewith.
Figure 5B:
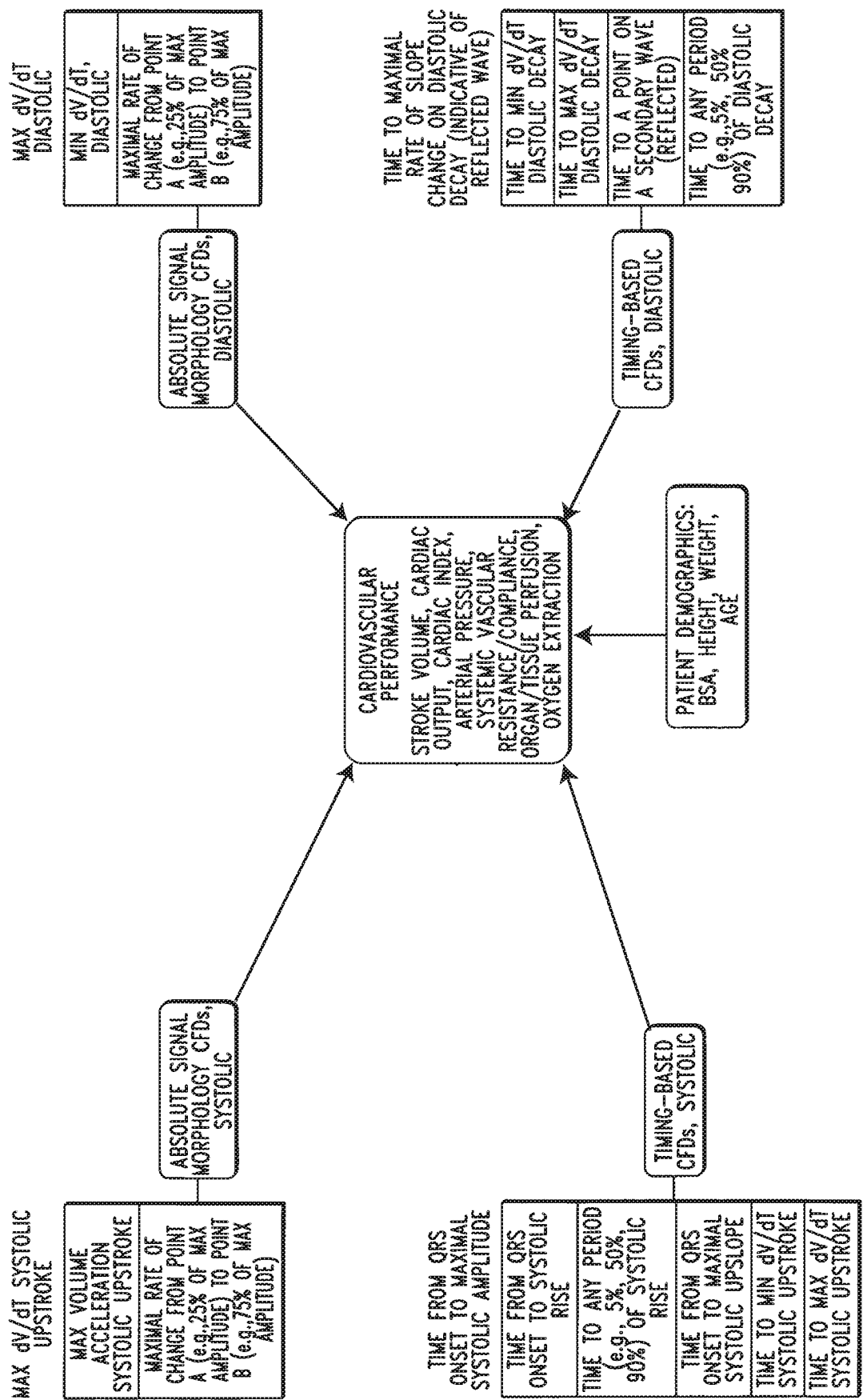
FIG. 5B is a schematic illustration of cardiac function determinants and the cardiac parameters associated therewith using a site 1 to site 2 comparisons of timing-based and absolute signal morphology-based CFDs.

As illustrated in prior art FIG. 5A, the cardiac function determinants can affect one of the cardiac parameters or multiple cardiac parameters, e.g. contractility and afterload. The use of various signals and data according to various embodiments of the present invention that may be used to compute cardiovascular performance is shown in greater detail in FIG. 5B, which indicates, for example, parameters (such as patient demographics) and measurements (such as dV/dt, and the times between measured occurrences) that may be used to determine the cardiovascular performance of a patient. The various parameters and measurements are defined and discussed in detail subsequently.

Figure 6:
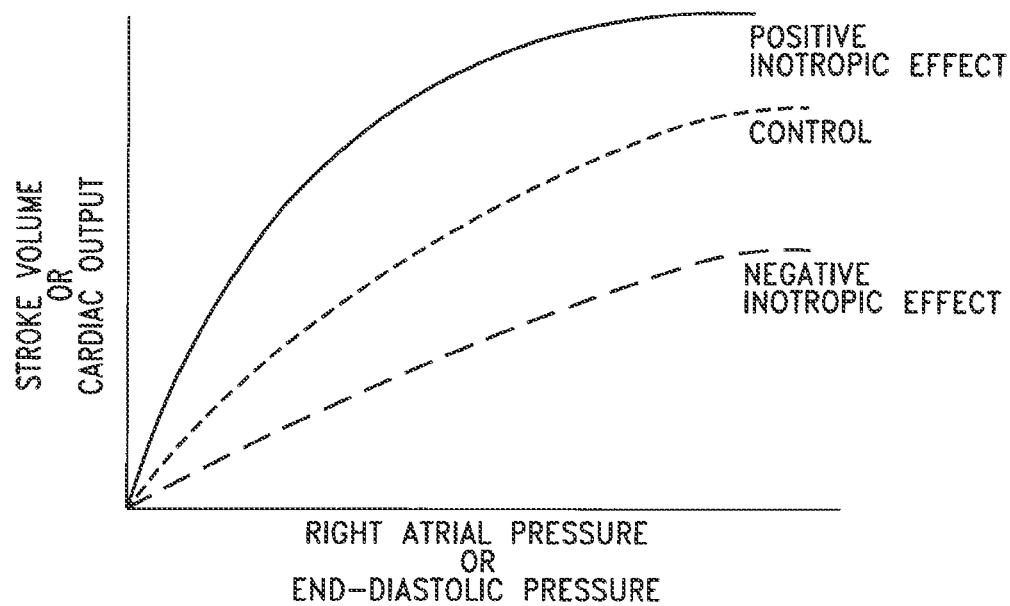
FIG. 6 is a graphical illustration of the relationship between cardiac output and left ventricular end diastolic volume based on the Frank-Starling principal.

Referring now to FIGS. 6-10, there are shown graphically illustrations of the effects of left ventricular end diastolic volume, venous return, right atrial pressure, central venous pressure, and total peripheral resistance on cardiac output. Referring first to FIG. 6, there is shown a graphical illustration of the relationship between cardiac output and left ventricular end diastolic volume (or between cardiac stroke volume and right atrial pressure) based on the Frank-Starling principal.

The Frank-Starling principal is based on the length-tension relationship of the myocardial or ventricular muscle within the ventricle. If ventricular end volume is increased, it follows that the ventricular muscle fiber length also increases, which results in increased muscle tension.

Accordingly, as illustrated in FIG. 6, cardiac output can be directly related to end diastolic volume or venous return, which is a key determinant of preload. Thus, when the heart rate is constant, cardiac output can be deemed directly related to preload (up to a defined point).

As is well known in the art, central venous pressure is generally deemed a good approximation of right arterial pressure (i.e. $CFD_m$), which, in turn, is a major determinant of right ventricular end diastolic volume (or the preload of the right ventricle). Referring to FIG. 6, it can, however, be seen that cardiac output can vary significantly with the same right arterial pressure.

FIG. 6 thus demonstrates that when right atrial pressure (i.e. preload) remains constant, cardiac output can still be affected by changes in contractility, afterload and, of course, heart rate.

Figure 7:
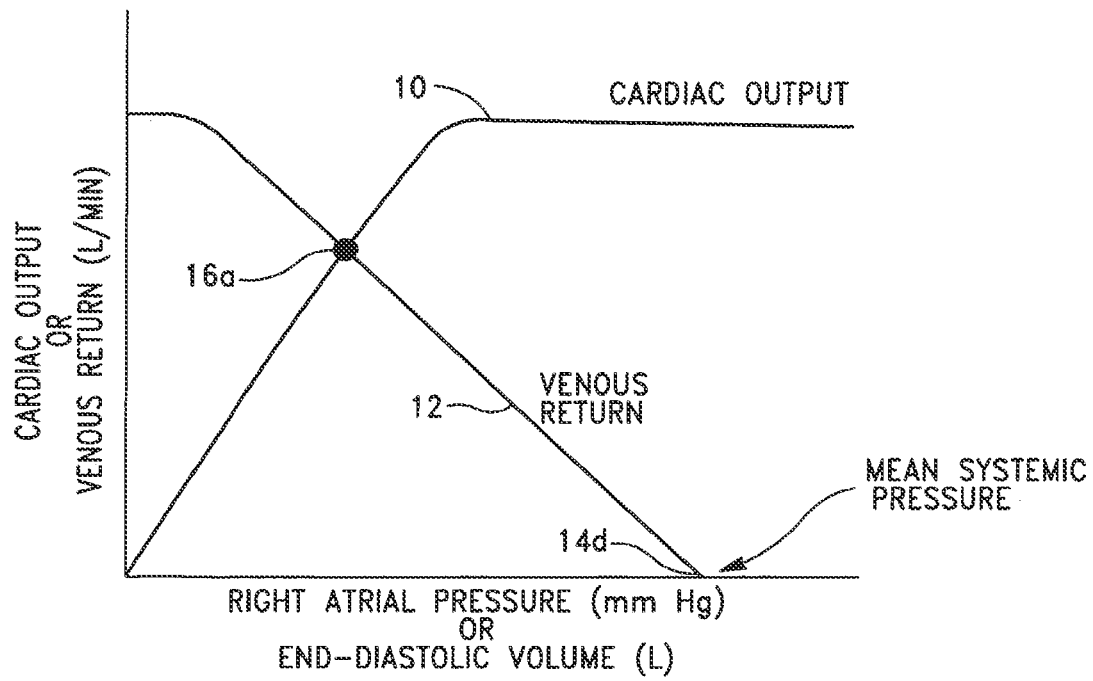
FIG. 7 is a graphical illustration of cardiac output and venous return as a function of end diastolic volume or right atrial pressure.

Referring now to FIG. 7, there is shown a graphical illustration of cardiac output and venous return as a function of end diastolic volume or right atrial pressure; curve 10 representing the Frank-Starling relationship of cardiac output as a function of end diastolic volume (i.e. $CFD_N$), and curve 12 representing the relationship between blood flow in the vascular system (i.e. venous return) and right atrial pressure (i.e. $CFD_M$).

As illustrated in FIG. 7, mean systemic pressure is deemed the point where the venous return curve 12 intersects the x-axis (denoted "14d"). At this point, the pressure is equal throughout the circulatory system.

Where the Frank-Starling and venous return curves 10, 12 intersect (denoted "16a") is deemed the equilibrium point, i.e. the point where cardiac output is equal to venous return.

As reflected in FIG. 7, cardiac output can increase or decrease with shifts or changes in the Frank-Starling and venous return curves 10, 12 and, hence, the relationships reflected thereby.

Figure 8:
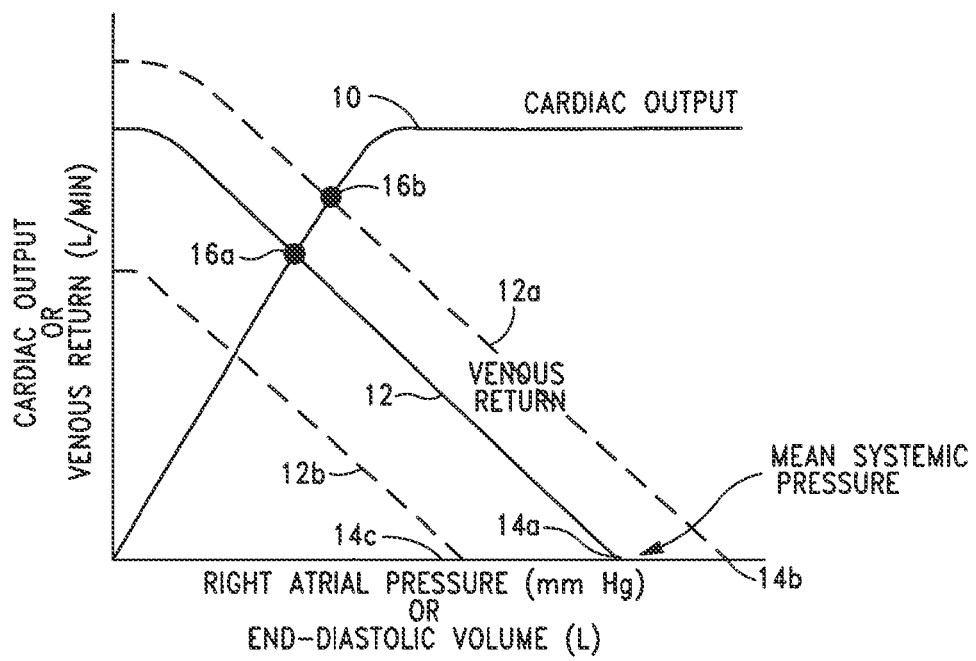
FIG. 8 is a further graphical illustration of the cardiac output and venous return relationships shown in FIG. 6, illustrating the effect of an increase in blood volume on the mean systemic pressure.

Referring now to FIG. 8, there is shown a further graphical illustration of the Frank-Starling and venous return relationships shown in FIG. 7, illustrating the effect of an increase in blood volume on the mean systemic pressure.

As is well known in the art, mean systemic pressure is affected by blood volume and venous compliance. As illustrated in FIG. 8, mean systemic pressure increases (i.e. x-axis intersection point moves from point 14a to point 14b) with an increase in blood volume and/or a decrease in venous compliance.

The venous return or vascular function curve 12 thus shifts to the right (shown by dashed line and denoted "12a"), illustrating an increase in cardiac output and right atrial pressure. The equilibrium point 16a also shifts (to point 16b).

Conversely, mean systemic pressure decreases with decreases in blood volume and/or an increase in venous compliance (x-axis intersection point moves from point 14a to 14c). The venous return curve 12 thus shifts to the left (shown by dashed line and denoted "12b") illustrating a decrease in cardiac output and right arterial pressure.

Figure 9:
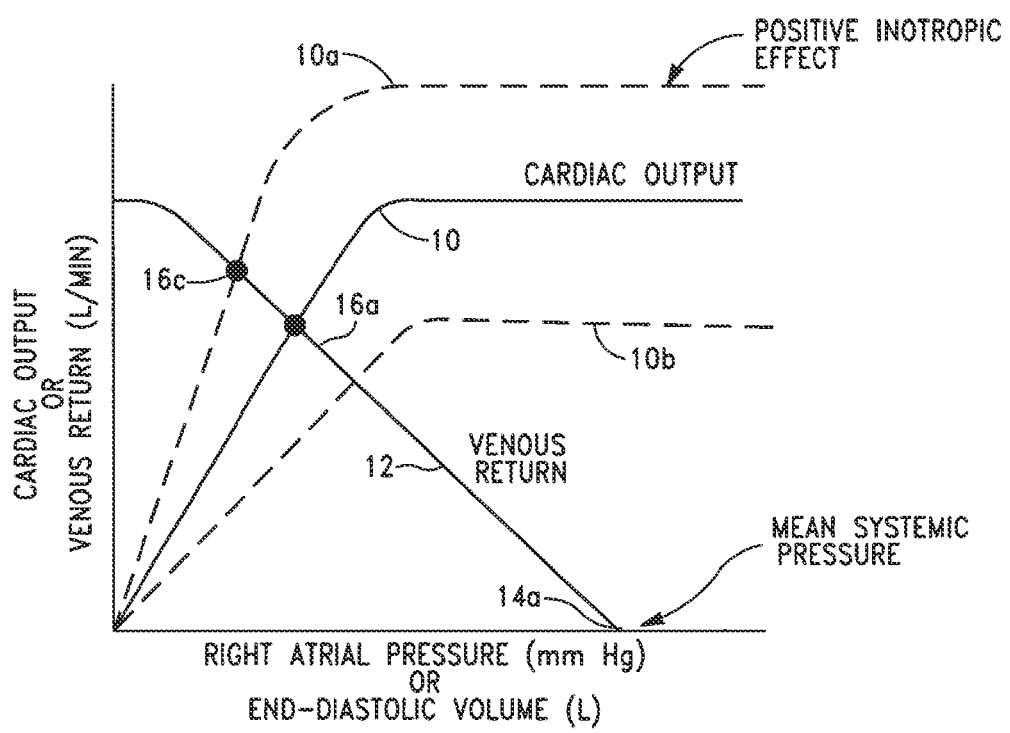
FIG. 9 is another graphical illustration of the cardiac output and venous return relationships shown in FIG. 6, illustrating the effects of inotropic changes on cardiac output.

Referring now to FIG. 9, there is shown another graphical illustration of the Frank-Starling and venous return relationships shown in FIG. 7, illustrating the effects of inotropic changes on the Frank-Starling curve 10.

As is well known in the art, contractility is based on various autonomic mechanisms and certain drugs, e.g., digitalis. As illustrated in FIG. 9 (and FIG. 6) positive inotropic agents, such as digoxin, will increase contractility and, hence, cardiac output (denoted by dashed line "10a"). The new equilibrium point 16c reflects an increased cardiac output and a lower atrial pressure, i.e. more blood being ejected from the heart with each beat.

As further illustrated in FIG. 9 (and FIG. 6) negative inotropic agents have an opposite effect; decreasing contractility and cardiac output (denoted by dashed line "10b"). Right atrial pressure also increases.

Figure 10:
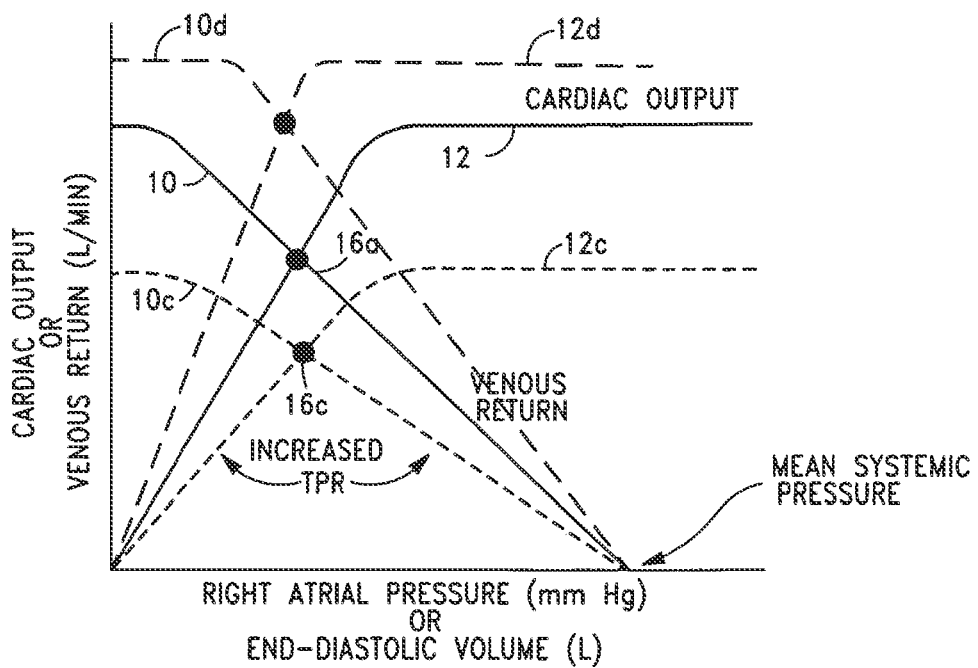
FIG. 10 is yet another graphical illustration of the cardiac output and venous return relationships shown in FIG. 6, illustrating the effects of changes in total peripheral resistance on cardiac output and venous return.

Referring now to FIG. 10, there is shown yet another graphical illustration of the Frank-Starling and venous return relationships shown in FIG. 7, illustrating the effects of changes in total peripheral resistance on the Frank-Starling and venous return curves 10, 12.

As is well known in the art, total peripheral resistance is based on the resistance of the arterioles. An increase in total peripheral resistance will thus cause blood to be retained on the arterial side of the circulatory system, increasing the aortic pressure or force necessary to eject blood from the ventricles. As illustrated in FIG. 10, the Frank-Starling and venous return curves 10, 12 will thus shift downward (denoted curves 10c and 12c, respectively), reflecting a decrease in cardiac output and venous return. However, the right atrial pressure remains the same.

A decrease in total peripheral resistance will shift the Frank-Starling and venous return curves 10, 12 upward (denoted by curves "10d" and "12d", respectively), reflecting an increase in cardiac output and venous return. The right atrial pressure similarly remains the same.

FIGS. 6-10 thus demonstrate the interrelated effects of preload, afterload and contractility determinants on cardiac output. Applicants thus recognized that an accurate determination of cardiac performance; particularly, cardiac stroke volume and output, mandates the determination and use of determinants associated with each cardiac parameter, i.e. preload, contractility and afterload.

Accordingly, in a preferred embodiment of the invention, the methods and associated algorithms for determining cardiac and/or cardiovascular performance (CP), e.g. systemic vascular resistance, degree of stenosis, blood volume, arterial pressure, hematocrit, oxygen delivery, stroke volume (SV), which, in combination with heart rate (HR), is commonly used as cardiac output (CO), are based on at least one cardiac determinant (or cardiac function determinant) associated with or at least in part, reflective of preload, contractility and afterload, i.e.

$$CP = f(CFD_x; CFD_y; CFD_z) \qquad \text{Eq. 1}$$

where: $CFD_x$ is a cardiac function determinant associated with preload, e.g., $CFD_1$ (see FIG. 4); $CFD_y$ is a cardiac function determinant associated with contractility e.g., $CFD_5$; $CFD_z$ is a cardiac function determinant associated with afterload, e.g., $CFD_{11}$; and $f(CFD_x; CFD_y; CFD_z)$ is an empirical relationship between $CFD_x$, $CFD_y$, and $CFD_z$.

In a preferred embodiment of the invention, the methods and associated algorithms for determining cardiac performance are based on multiple cardiac function determinants associated with or at least in part, reflective of each cardiac parameter, i.e. preload, contractility and afterload, e.g., $$SV = f_{co}(CFD_{(c)x}; CFD_{(c)y}; CFD_{(c)z}) \qquad \text{Eq. 2}$$

where: SV is a cardiac stroke volume; $CFD_{(c)x}$ is a combination of cardiac function determinants associated with preload, e.g., $CFD_1$-$CFD_2$-$CFD_3$ (see FIG. 4); $CFD_{(c)y}$ is a combination of cardiac function determinants associated with contractility, e.g., $CFD_5$-$CFD_6$-$CFD_7$; $CFD_{(c)z}$ is a combination of cardiac function determinant associated with afterload, e.g., $CFD_{11}$-$CFD_{12}$-$CFD_{13}$; and $f_{co}$ is a combination of empirical relationships or mathematical functions that combine $CFD_{(c)x}$, $CFD_{(c)y}$, and $CFD_{(c)z}$.

In one embodiment, wherein the desired cardiac performance is systolic blood pressure, a minimum of three cardiac function determinants are preferably employed for a complete description and accurate determination of blood pressure. The following is illustrative (i) when a patient is hypovolemic, then preload is reduced, stroke volume is smaller, ejection is easier and faster, less pressure is developed, (ii) when an inotrope is administered, contractility is increased, and at unchanged compliance and resistance of the vasculature, blood pressure in increased, (iii) when a vasopressor is administered, the resulting arteriolar restriction results immediately in increased afterload and thus, increased blood pressure.

In one embodiment of the invention, the cardiac function determinant associated with preload, i.e. $CFD_x$, is determined from the width measured in seconds of the ejection phase of the plethysmogram data; the cardiac function determinant associated with contractility, i.e. $CFD_y$, is determined from the normalized maximal rate of change of the systolic upslope of the ejection phase and measured in 1/seconds; the cardiac function determinant associated with afterload, i.e. $CFD_z$, is determined from the normalized rate of change of the systolic upslope at the inflection point and measured in 1/seconds also. In one embodiment, the three cardiac function determinants are mathematically connected by multiplication.

In another embodiment, wherein the desired cardiac performance is systemic vascular resistance (i.e. the overall resistance to blood flow by the systemic vasculature), a minimum of three cardiac function determinants are similarly preferably employed. However, since systemic vascular resistance is often determined as the ratio of mean arterial pressure (MAP) divided by cardiac output (CO), the three sets of cardiac function determinants are employed for a complete description and accurate determination of MAP and CO. The following is illustrative: MAP is determined in a fashion analogous to systolic blood pressure and CO is determined as the product of SV and heart rate.

According to the invention, where the desired cardiac function is blood volume, an estimate can be obtained from MAP and compliance.

Where the desired cardiac function is perfusion, as defined by oxygen delivery to the tissue and extraction, the following is illustrative: arterial oxygen saturation and venous oxygen saturation via ear lobe tonometry in combination with cardiac output.

To the extent that the cardiac function determinants, e.g. $CFD_{(c)x}$, are composed of more than one measured cardiac function determinant, e.g. $CFD_1$, $CFD_2$, $CFD_3$, in one embodiment of the invention, mathematical cross-terms or correction factors are introduced in Equation 2 to minimize the effect of lesser contributors to any single CFD.

By way of example, to account for the contribution of afterload to the measured $CFD_1$ for desired contractility, $CFD_{(c)x}$ in Equation 2 is preferably modified as follows:

$$CFD_{(c)x} = a*(CFD_1 - (b*(CFD_2/CFD_3))) \qquad \text{Eq. 3}$$

where: a and b=correction factors (or predetermined variables).

According to the invention, multiple correction factors can be applied to any measured CFD. In order to achieve an accurate estimate of the desired CP, the corrected CFDs are mathematically treated as combinations, either as closed form equations or numerical values.

By way of example, to account for the contribution of preload, measured as $CDF_4$, on the measured parameter $CFD_2$ Equation 3 is represented as follows:

$$CFD_{(c)x} = a*(CFD_1 - (b*(c*(1-CDF_4)*CFD_2)/CFD_3)) \qquad \text{Eq. 4}$$

As discussed in detail herein, the algorithms of the invention, such as Equation 2 above, can be deemed closed loop, interactive systems, i.e. the determination of cardiac performance is based on the interactive relationship by and between multiple cardiac function determinants associated with or at least in part, reflective of each cardiac parameter.

According to the invention, the cardiac function determinants are preferably derived from at least three areas of data that are acquired from patient-technology interfaces. Preferably, the interfaces comprise sites, e.g. ears, fingers, that are readily accessible with non-invasive means to generate data relating to (i) absolute and relative times of selective physiological signals, (ii) amplitudes of selective physiological signals and, in particular, time-variant changes of the signals, and (iii) relationships of physiological signal times and amplitudes obtained from different measurement sites.

In one embodiment of the invention, the physiological signals comprise electromagnetic radiation absorption measurements through tissue, and/or the determination of body-part size changes as the result of blood flow (i.e. plethysmographic measurements) and electrical measurements of the heart, as measured by an electrocardiogram ("ECG"). Electromagnetic radiation absorption measurements can include, but are not limited to, measurements of the absorption of light through the body, where the term "light" refers, without limitation, to electromagnetic radiation in the infrared or visible regions.

In a preferred embodiment of the invention, the plethysmographic measurements are acquired at two sites on the subject's body. In one embodiment of the invention, discussed in detail herein, the two sites comprise a point proximate the central circulation system, preferably, close to the heart, such as the nose, earlobe, neck, upper shoulder, chest, etc., and at a peripheral point on the body, such as a digit, hand, arm, leg, etc.

Figure 11:
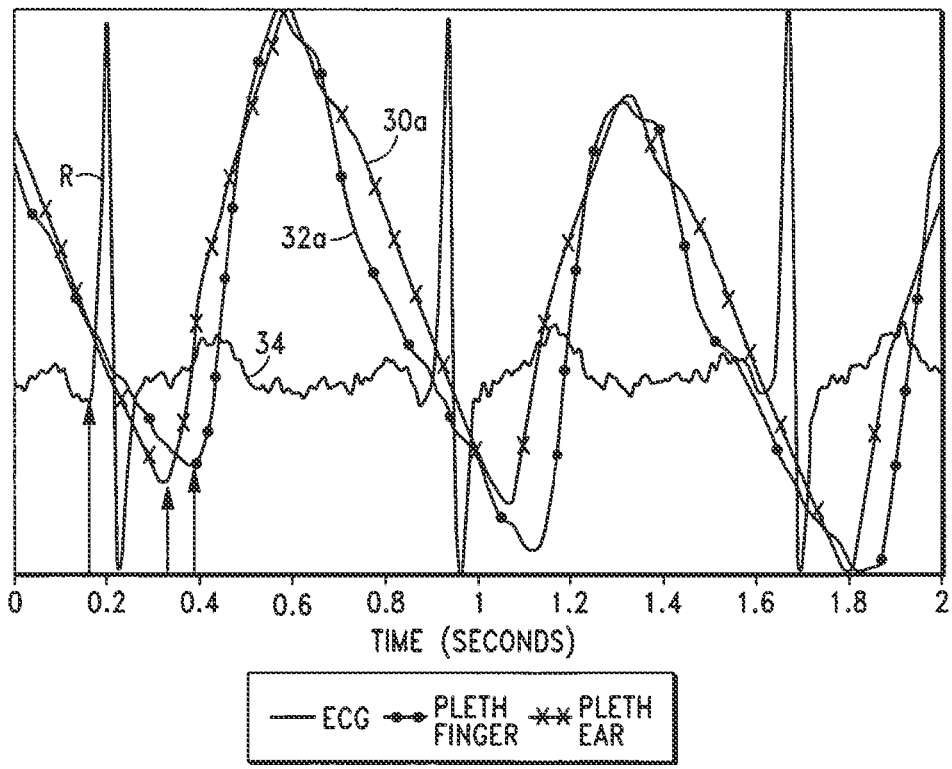
FIG. 11 are exemplar plethysmogram and ECG waveforms representing plethysmographic measurements at the ear, plethysmographic measurements at a finger, and electrical measurements of the heart.

According to the invention, the signals are employed to generate waveforms representing the measured parameter(s) over time. Referring now to FIG. 11, there are shown exemplar waveforms representing (i) plethysmographic measurements at the ear 30a, (ii) plethysmographic measurements at a finger 32a, and (iii) electrical measurements of the heart, i.e. ECG waveform 34.

In the noted illustration, the shapes of the plethysmograph waveform representing the plethysmographic measurements at the ear 30a and the plethysmograph waveform representing the plethysmographic measurements at a finger 32a are similar, e.g., waveform curvature proximate peak amplitudes. As will be appreciated by one having ordinary skill in the art, the noted similarities reflect a measure of compliance in the vasculature that can be mathematically related to afterload.

Figure 12:
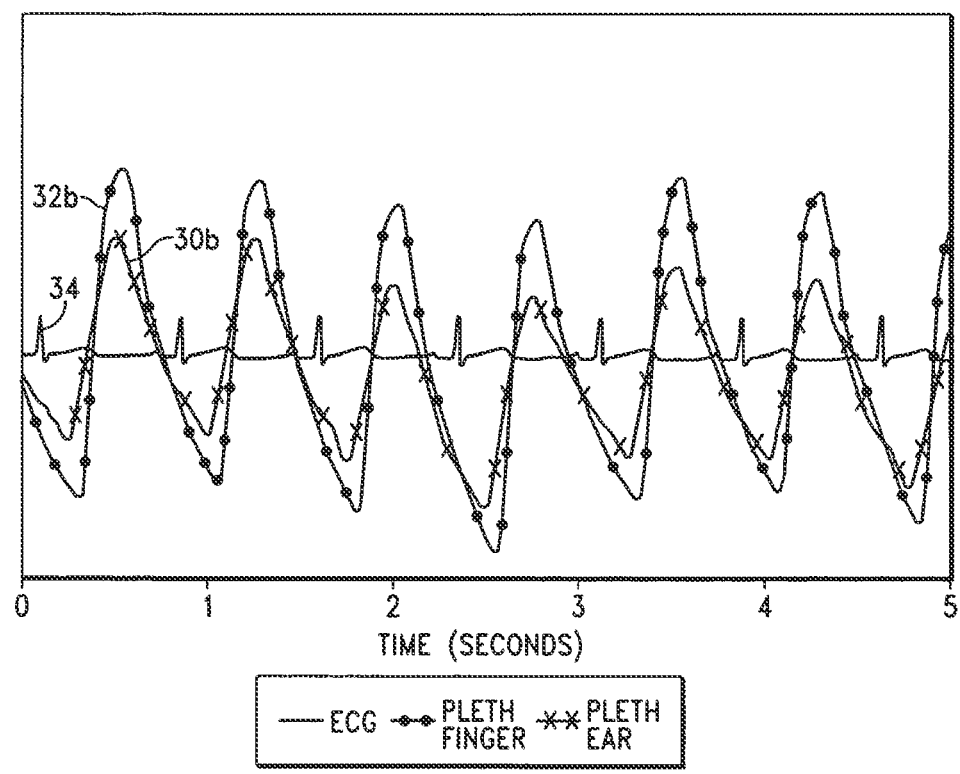
FIG. 12 are further exemplar plethysmogram and ECG waveforms representing plethysmographic measurements at the ear, plethysmographic measurements at a finger, and electrical measurements of the heart.

However, as will also be appreciated by one having ordinary skill in the art, the waveforms 30a, 32a can, and in many instances will, be quite different, see, e.g., waveforms 30b, 32b in FIG. 12. The differences, such as slope(s), amplitudes, etc., can reflect compliance of the aorta and the large arteries.

Referring back to FIG. 11, the ECG waveform comprises a complex waveform having several components that correspond to electrical heart activity. As discussed in detail below, a significant component is the QRS component or complex, which relates to the initiation of ventricular heart contraction.

The R wave portion (or component) of the QRS complex is typically the steepest wave therein, having the largest amplitude and slope, and is often used to determine the onset of cardiovascular activity, i.e. initiation of isovolumic contraction (see FIG. 3). The arterial pulsed blood pulse flows mechanically and its appearance in any part of the body typically follows the R wave of the electrical heart activity by a determinable period of time that remains essentially constant for a given patient. See, e.g., Goodlin et al., "Systolic Time Intervals in the Fetus and Neonate", Obstetrics and Gynecology, vol. 39, No. 2 (February 1972) and U.S. Pat. No. 3,734,086.

The methods and associated algorithms for determining the cardiac function determinants and cardiac performance therefrom will now be described in detail. It is, however, understood that, in many instances, various, multiple cardiac characteristics and events can be employed to derive the cardiac function determinants. The preferred and/or selected cardiac characteristics and events, and cardiac function determinants derived therefrom, that are employed in the methods and associated algorithms, described herein, should thus not be deemed limiting in any manner.

It is further understood that selected cardiac characteristics and events, and cardiac function determinants derived therefrom, can be derived in accordance with methods and systems disclosed in Co-Pending U.S. application Ser. No. 11/418,937, filed 4 May 2006, which published as US Patent Application Publication No. 2007-0260132 A1 on Nov. 8, 2007; U.S. application Ser. No. 11/700,328, filed 30 Jan. 2007, which published as US Patent Application Publication No. 2008-0183232 A1 on Jul. 31, 2008; and U.S. application Ser. No. 12/011,122, filed 23 Jan. 2008, which issued as U.S. Pat. No. 8,834,382 on Sep. 16, 2014; which are expressly incorporated by reference herein in their entirety.

Absolute and Relative Times of Physiological Signals

In accordance with at least one embodiment of the invention, cardiac function determinants associated with preload, contractility and afterload are derived from absolute and relative signal time periods reflecting the ejection period (EP) and pulse transit time (PTT). In some embodiments of the invention, the relative signal shapes of peripheral and central plethysmograms, such as pulse widths and the time lag between the noted plethysmograms, are also employed to derive the cardiac function determinants.

In a preferred embodiment of the invention, the signals reflecting the ejection period and pulse transit time comprise ECG signals. While it is possible to utilize any part of a measured and synchronously collected ECG signal for timing purposes of events at distal locations, such as at the ear or finger, it is preferable to utilize the QRS complex, since it defines the electrical onset of ventricular contraction. In addition, the QRS complex is typically the component of the signal with the largest signal to noise ratio (SNR) and, therefore, the most accurate to use for defining the zero point in time as the start of the pulse cycle.

Figure 13:
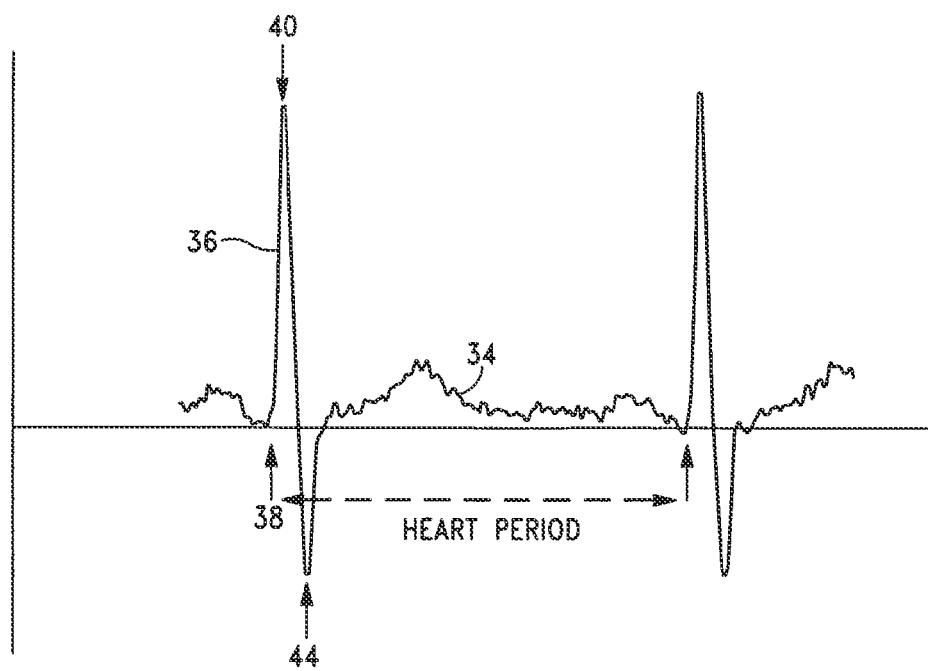
FIG. 13 is an exemplar QRS complex or component of an ECG waveform.

Referring now to FIG. 13, there is shown an exemplar QRS complex (denoted generally "36") of ECG signal 34. As illustrated in FIG. 13, the QRS complex 36 includes the Q component 38, R component 40 (discussed above), and S component 44.

As is well known in the art, the QRS complex represents ventricular depolarization. The duration of the QRS complex is normally in the range of approximately 0.06-0.1 sec. This relatively short duration indicates that ventricular depolarization normally occurs very rapidly.

A prolonged QRS complex (i.e. >0.1 sec) is indicative of abnormal conduction within the ventricles. This can occur with bundle branch blocks or whenever a ventricular foci (abnormal pacemaker site) becomes the pacemaker driving the ventricle. Such ectopic foci virtually always results in impulses being conducted over slower pathways within the heart, thereby increasing the time for depolarization and the duration of the QRS complex.

In one embodiment of the invention, the method for identifying the time point associated with the onset of ventricular depolarization preferably includes first locating the maximal absolute deviation of the QRS complex from the baseline. As illustrated in FIG. 12, the peak deviation from baseline defines the R component 40 of the QRS complex 36.

After locating the maximal absolute deviation of the QRS complex from the baseline, the Q component of the QRS component is then detected (i.e. time point associated therewith). According to the invention, the Q component of the QRS component is defined as the maximal acceleration point from the baseline to the R component.

The S component of the QRS component is then detected (i.e. similarly, the time point associated therewith). According to the invention, the S component of the QRS component is defined as the maximal acceleration point post R component upon return near baseline.

According to the invention, the presence of a QRS complex can be identified by applying a band pass filter (i.e. 5 to 30 Hz) to the ECG signal, post spike removal; then detecting episodes, wherein the difference between the peak and the preceding baseline exceeds predefined absolute amplitude.

Figure 14:
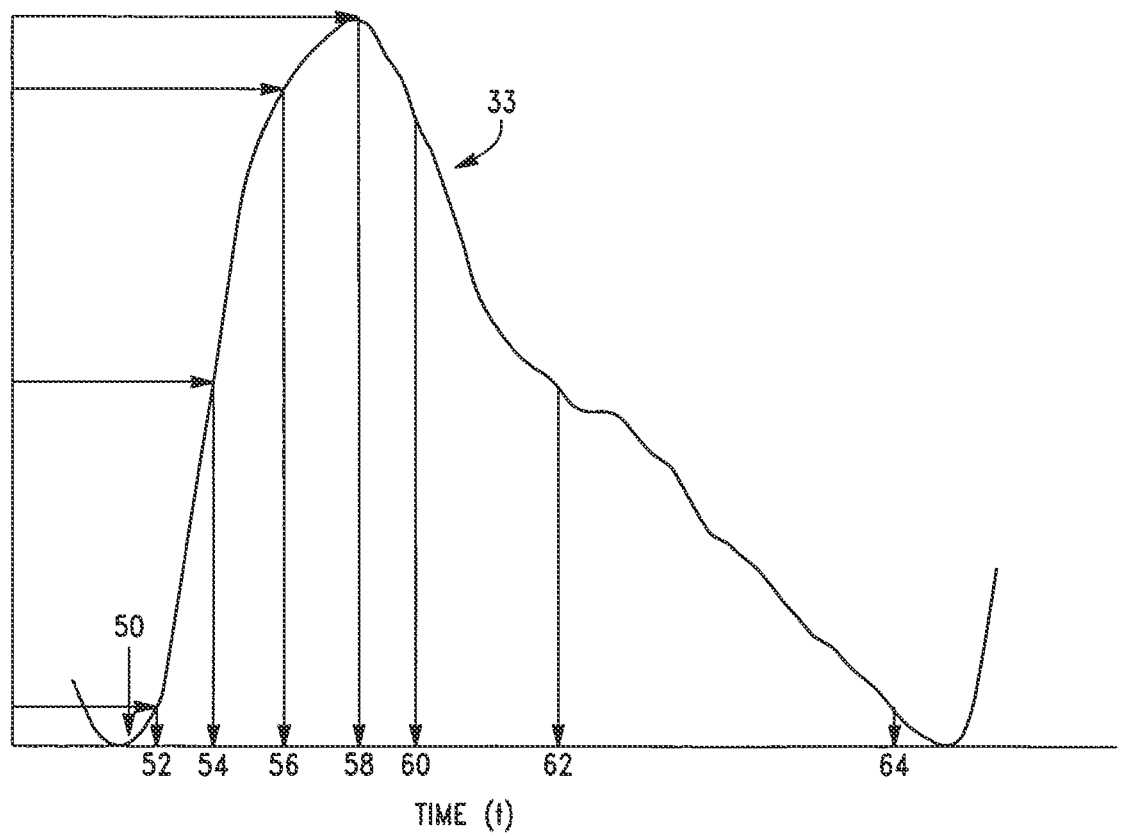
FIGS. 14 and 15 are further exemplar plethysmograms, showing seminal points thereon and time periods associated therewith.

According to the invention, the aforementioned QRS complex time points define the beginning of a pulse wave and enables accurate determination of times to other points of synchronously collected plethysmogram signals. Referring to plethysmogram 33 in FIG. 14, the times include, without limitation, the time to onset of the systolic rise (denoted "50"), the time to maximal systolic up-slope, the time to maximal systolic amplitude, i.e. time point associated with maximum volume during a cardiac cycle (denoted "58"), to any percentage of the systolic rise, such as 5%, 50%, or 90% of the maximal amplitude, i.e. time point associated with volume being 5% (denoted "52"), 50% (denoted "54") and 90% (denoted "56") of maximum volume during systolic rise, the time to any percentage of the diastolic decay, such as 5% (denoted "64"), 50% (denoted "62"), or 90% (denoted "60") of the maximal amplitude. Preferably, each of the noted amplitudes is defined by and, hence, measured as the difference to the diastolic baseline between pulses.

Figure 15:
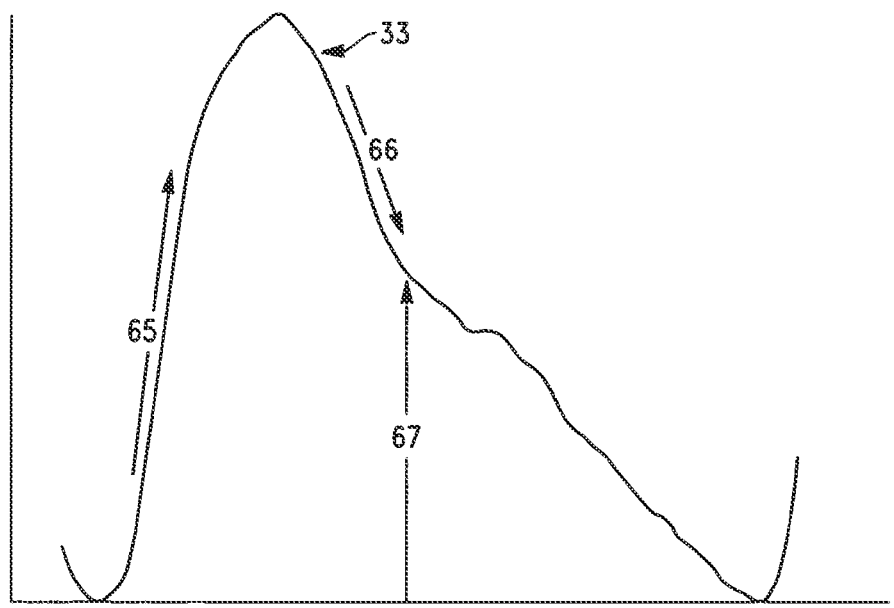

Referring to FIG. 15, the times also include the time to any point of inversion or slope change on either side of the pulse wave (represented by plethysmogram 33), such as the maximum slope (dV/dT) during systolic rise (denoted "65") and the minimum slope (dV/dT) during diastolic decay (denoted "66"), and the time to any point on a secondary peak, such as a reflected wave component or another premature pulse wave.

The time point at the first maximal rate of slope change on the diastolic decay side (denoted "67") is a marker for the end of the systolic phase and also indicates the beginning of a reflected wave.

In one embodiment of the invention, the times of interest (or cardiac event times) include: the time point reflecting the onset of a pulse wave; the time point that the amplitude of the systolic upstroke is at 5% of the maximal amplitude; the time point to the maximal amplitude of the first systolic peak, as a measure of systolic upstroke interval; the time point of maximal rate of increase of amplitude; the time point at 50% of maximal amplitude on either side of the systolic peak; and the time point at 90% of maximal amplitude on either side of the systolic peak.

As will readily be appreciated by one having ordinary skill in the art, the accurate determination of the time point reflecting the onset of the pulse wave is useful for calculating time differences to other features of the same pulse wave, as well as for calculating delays between wave arrival times at different measurement sites, such as an ear and finger.

As will also be readily appreciated by one having ordinary skill in the art, the time point of maximal rate of increase of amplitude represents the strength of contractility with a minor influence of compliance. The noted phenomena is based on the understanding that at low blood output, the downstream vasculature poses little resistance to the oncoming pressure wave, such that all pressure can be converted readily to volume flow. Thus, contractility is largely the determinant of the initial upstroke of the measured systole.

It is also well established that the time point at 50% of maximal amplitude on either side of the systolic peak is a measure of resistance and compliance, which is effected by variable vasoconstriction or/and variably elastic vasculature.

In combination with amplitude measurements, the total area under the curve ("AUC") is calculated and used for normalizing individual measured plethysmographic parameters. Combined mathematically, this represents the major component contributing the determination of afterload.

As will further be appreciated by one having ordinary skill in the art, the time periods from (i) onset of the systole to its maximum, (ii) onset of systole to dichrotic notch, (iii) onset to 90% of max on the diastolic down stroke, and (iv) 50% of maximum on the upstroke to 50% on the down stroke are all considered useful measures for determining ejection period. The noted time periods are deemed reliably measurable quantities that define the period of ventricular ejection.

Amplitudes of Signals and Time-Variant Changes Thereof

In accordance with at least one embodiment of the invention, cardiac function determinants associated with preload, contractility and afterload are derived from amplitudes of signals and, in particular, time-variant changes of the signals.

According to the invention, the contour profile of a plethysmogram is preferably defined by selecting measured amplitude parameters that are independent of uncontrolled variables, such as sensor type and placement, blood pressure and compliance/resistance condition of the vasculature. This is preferably accomplished by normalizing amplitudes, slopes and changes of slopes by the total area under the curve (AUC) between diastolic minima, or by dividing by AUC, as defined by other time points, as described above, and a baseline, such as defined by one or more diastolic minima.

In one embodiment of the invention, the method employed to normalize the amplitudes comprises dividing the slope parameter by maximal pulse amplitude.

In one embodiment of the invention, the amplitudes and slope parameters of interest comprise: (i) the maximal rate of increase of systolic up-slope (denoted "65" in FIG. 15) and (ii) the rate of increase from one specific percentage of the maximal systolic amplitude to another specific percentage, e.g., 25% to 75% of the maximal systolic amplitude.

According to the invention, a similar set of slope parameters can be derived from the diastolic decay, such as the maximal rate of change from any predefined percentage point of the diastolic decay to another, such as 100% to 10% or 90% to 50% of the maximal amplitude.

According to the invention, other amplitudes and slope changes to any point on the plethysmogram can, and in many instances will, reflect additional relevant information. Such information can comprise, for example, information relating to secondary peaks, such as a reflected wave component or another premature pulse wave.

Preferably, each of the amplitudes referenced above are measured as the difference from a defined point to one diastolic minimum, such as the diastolic minimum of a preceding pulse wave or, alternatively, a diastolic baseline that is calculated from two or more diastolic minima between pulses.

In one embodiment of the invention, the times of interest (or cardiac event times), which can be used to define the corresponding amplitudes at those time points, thus include: The time point reflecting the maximal rate of increase of amplitude; The time point reflecting 50% of maximal amplitude on either side of the systolic peak; and The time point reflecting the maximal rate of slope change on the diastolic decay side of the plethysmogram.

In one embodiment of the invention, contour analysis is employed to derive cardiac function determinants associated with preload, contractility and afterload.

According to the invention, for optimal precision of a large number of clinical data, key slope parameters are preferably selected (as described above) and utilized in empirical relationships or mathematical calculations that employ a form of multivariate analysis.

It is also envisioned that complete wave shape comparisons are enabled by large patient data bases. Thus, statistical correlations of individual wave shapes with individual patient conditions can be determined for the delivery of a diagnosis.

As will be readily appreciated by one having ordinary skill in the art, the slope parameters described above and employed in various embodiments of the invention are affected to a different degree by preload, contractility and afterload. However, by virtue of the methods and associated algorithms of the invention, it is possible to employ empirical or mathematical combinations that enable corrections, such as the effect of afterload due to aortic compliance on the measured max upstroke slope parameter. The correcting parameter in this example can be the max diastolic slope, which is largely determined by the condition of the vasculature. In principle, every measured parameter in the area of contour analysis can thus be corrected for the presence of minor contributors.

By way of example, the initial systolic upstroke, i.e. the slope of the increase of amplitude over time, is mostly influenced by contractility. However, as the aorta and larger arteries are expanded by the pressure wave, their compliance is less and the observed systolic slope is decreased. As is well known in the art, compliance is a patient-specific independent parameter.

For proper estimation of contractility, the contribution by compliance is thus eliminated from the measured initial systolic upstroke parameter. Such corrections can be achieved by utilizing a transfer function, as disclosed below.

Relationships of Times and Amplitudes Obtained from Different Measurement Sites

In accordance with at least one embodiment of the invention, cardiac function determinants associated with preload, contractility and afterload are derived from relationships of times and amplitudes, which are obtained from different measurement sites.

Figure 16:
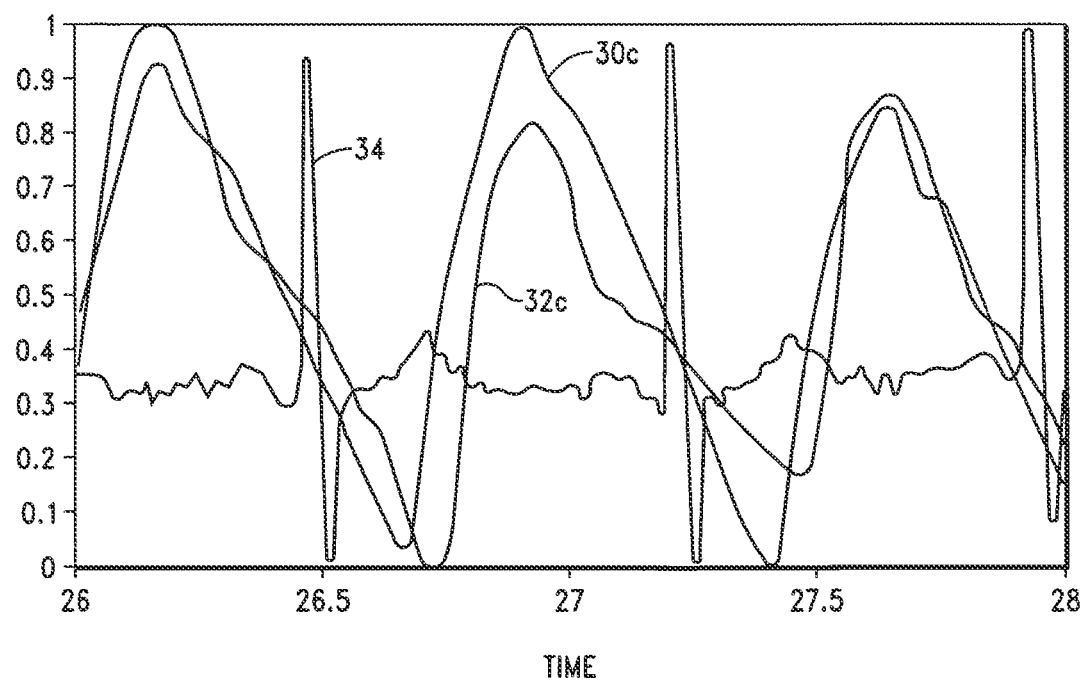
FIG. 16 are further exemplar plethysmogram and ECG waveforms representing plethysmographic measurements at the ear, plethysmographic measurements at a finger, and electrical measurements of the heart.

Referring now to FIG. 16, there are shown further exemplar waveforms representing (i) plethysmographic measurements at the ear 30c, (ii) plethysmographic measurements at a finger 32c, and (iii) electrical measurements of the heart, i.e. ECG waveform 34.

According to the invention, the plethysmographic measurements at the ear 30c and finger 32c can be derived via the methods and devices disclosed in U.S. Application No. 60/966,594 (filed 28 Aug. 2007), 61/000,428 (filed 25 Oct. 2007), and 61/063,279 (filed 31 Jan. 2008); which are incorporated by reference herein in their entirety.

In this instance, there are significant and information-containing differences between the shapes and timing of the same systolic or pulse wave when measured at the different sites, i.e. ear lobe and fingertip. As illustrated in FIG. 15 (and FIG. 11), the time of onset of the pulse wave at the ear is earlier, since the distance traveled by the pulse wave to the ear, as compared to the finger, is shorter. Yet, the contour of the pulse wave at the finger is more crested, i.e. the systolic rise and decay are increased, and narrower, because of the greater effects of the narrowing vasculature and the longer travel distance of the pulse wave.

According to the invention, waveform parameters, such as those discussed above, can thus be extracted from different plethysmograms, i.e. obtained from two or more different body sites, such as foot and hand or toe and forehead or as preferred, finger and ear lobe. The differences between comparable measured parameters from different sites carry additional information about the condition of the arterial tree transited by the pulse wave. In a preferred embodiment, such information is extracted by comparing the shape of the waveform, i.e. plethysmogram, from one site to the shape of the waveform from the other site.

The waveform parameters, which are preferably derived from time periods associated with the signals, as well as from normalized waveform amplitudes, are then employed in empirical relationships or mathematical combinations to extract specific information about lag times of pulse arrival and differences of slopes.

As indicated above and illustrated in FIGS. 11 and 15, a pulse wave that has traveled a longer distance through the narrowing arterial tree is typically more crested. Thus, according to the invention, the degree to which that occurs can be mathematically expressed as the ratio of two waveform parameters, such as the maximal slope on either side of the pulse wave.

According to the invention, a mathematical transfer function can also be derived and employed, which expresses the transformation of one pulse wave shape associated with one site into the other wave shape associated with the other site. The coefficients that provide the best fit of the data contain the information about the effects of a particular vascular condition on a specific wave shape output from a ventricle.

Any such complex transfer function, which can be as simple as the ratio disclosed above, carries largely information solely about large arterial compliance and resistance by the smaller arteries. The noted information is thus directly useful for deriving empirical or mathematical relationships for afterload.

By way of example, given plethysmogram signals A(t) and B(t), in one embodiment of the invention, the transfer function is defined by a Volterra series expansion, i.e.

$$B(t) = \int_0^\alpha T_n(\tau_1 \ldots \tau_n) A(t-\tau_1) \ldots A(t-\tau_n) d\tau_1 \ldots d\tau_1 \qquad \text{Eq. 5}$$

where:
$T = \{T_0, T_1, T_n, \ldots\}$, and
wherein the $n^{th}$ term of the series is deemed the $n^{th}$-order Volterra transform, and the function $T_n(\tau_1 \ldots \tau_n)$ comprises the $n^{th}$-order Volterra kernel.

As will readily be appreciated by one having ordinary skill in the art, the kernels are essentially higher-order impulse response functions, and (as in the case of a linear input-output system,) carry information about the transmission of energy from input (A) to output (B).

In one embodiment of the invention, the series is preferably truncated at the second order (for the sake of tractability), i.e.

$$B(t)=T_0+\int_0^\alpha T_1(\tau_1)A(t-\tau_1)d\tau_1+\int_0^\alpha T_2(\tau_1,\tau_2)A(t-\tau_1)A(t-\tau_2)d\tau_1 d\tau_2 \quad \text{Eq. 6}$$

According to the invention, the kernels $\{T_0, T_1, T_2\}$ can be found via Fourier methods, or by a recursive least squares approach, and, in the case of plethysmogram signals, are hypothesized to encode physiological parameters, such as compliance and impedance of the vasculature between the points interrogated in pleth(A) and pleth(B). The nature of this encoding can be determined by computing in the case of pulsatile flow in a flexible tube, for which the system parameters are variable (and known). Given the mapping from {system/flow parameters} to {Volterra kernels}, the inversion of this process provides an effective means of extracting physiological data from the transfer function.

According to the invention, alternate approaches to the Volterra approach can also be employed, including, without limitation, the Volterra-Wiener model (similar to the Volterra model, but imposing orthogonality between the kernels of different orders), and polyspectra. Each of these techniques models nonlinear transforms among functions, and all have been applied successfully in the modeling of images (specifically, the problem of deblurring), electronic systems, and the physiology of vision (response of retinal ganglion cells).

The transform-function approach is both widely general and tractable for low-order systems. If the pair of plethysmogram signals carries information about the intervening vasculature, this method will expose it.

Alternatively, $n^{th}$ order polynomial fits can be applied to the plethysmogram signals from different sensing sites separately, followed by comparative analysis of the coefficients, such as the ratios of coefficients at the same order, e.g., ($c_1$ ear)/($c_1$ finger) of the $x^2$ terms.

EXAMPLES

According to the invention, selective cardiac time periods and waveform parameters, and cardiac function determinants derived therefrom (as described and discussed in detail above), are mathematically combined to determine cardiac performance. Illustrative are the following examples.

It is, however, understood that the examples are merely provided to enable those skilled in the art to more clearly understand and practice the present invention. The examples, thus, should not be considered as limiting the scope of the invention, but merely as being representative thereof.

Example 1

Referring now to Equation 7, there is shown a general empirical relationship of the invention that can be employed to derive an accurate estimation of cardiac stroke index (SI), i.e.

$$SI=\alpha*LVET/PEP*(1-\beta*((dv/dt_{e,s}/dv/dt_{f,s})*(dv/dt_{e,s}/dv/dt_{e,d}))) \quad \text{Eq. 7}$$

where: LVET=left ventricular ejection time; PEP=pre-ejection period; $\alpha$ and $\beta$=variable constants that are measurement system-specific; $dv/dt_{e,s}$=the maximal systolic upslope of the plethysmogram signal obtained at the ear; $dv/dt_{f,s}$=the maximal systolic upslope of the plethysmogram signal obtained at the finger; and $dv/dt_{e,d}$=the maximal diastolic down slope of the plethysmogram signal obtained at the ear.

In this example, the Stroke Index (SI) is determined (via Equation 7) by the product of three terms or determinants: (i) the ratio of ejection time from onset at the max change of systolic upslope to the max change of rate of slope in the diastolic down-slope divided by pre-ejection period, (ii) the ratio of max up-slope ear to max upslope of finger plethysmogram, and (iii) the ratio of max upslope to max downslope of ear plethysmogram.

The ejection period being derived as set forth in Co-pending U.S. application Ser. No. 12/011,122 (referenced above). The coefficients $\alpha$ and $\beta$ being derived experimentally for best data fit.

Referring now to Equation 8, below, there is shown the empirical relationship embodied in Equation 7 with illustrative client and measurement system-specific parameters, i.e.

$$SI=14.02*LVET/PEP*(1-0.3*((dV/dT_{e,s}/dV/dT_{f,s})*\text{Maximum}(1.5,(dV/dT_{e,s}/dV/dT_{e,d})))) \quad \text{Eq. 8}$$

where: $\alpha=14.02$; $\beta=(0.3)$; $dV/dT_{e,s}$ is calculated using systolic portion of the volumetric ear signal, normalized over a single pulse such that minimum=0 and Peak systole=1, $dV/dT_{e,s}=\text{MAXIMUM}(V_e(t)-V_e(t-0.05 \text{ seconds})/0.05 \text{ seconds}$; $dV/dT_{f,s}$ is calculated using systolic portion of the volumetric finger signal, normalized over a single pulse such that minimum=0 and Peak systole=1, $dV/dT_{f,s}=\text{MAXIMUM} (V_f(t)-V_f(t-0.05 \text{ seconds})/0.05 \text{ seconds}$; $dV/dT_{e,d}$ is calculated using diastolic portion of the volumetric ear signal, normalized over a single pulse such that minimum=0 and Peak systole=1, $dV/dT_{e,d}=\text{MINIMUM} (V_e(t)-V_e(t-0.05 \text{ seconds})/0.05 \text{ seconds}$; PEP is the pre-ejection period; and LVET=the time (seconds) between onset of systole until the time post peak systole that the volume returns to less than 50% maximum.

Example 2

A primary, uncorrected estimate of strength of contraction is obtained from the systolic upstroke interval as the difference of amplitudes between 75% and 25% divided by the maximal systolic amplitude; the derived strength of contraction serving as variable ($dv/dt_{e,s}$) in Eq. 7, above.

Example 3

An equivalent measure for strength of contraction as upstroke interval (as described in Example 1) is obtained by calculating the time difference of the QRS component to 75% of systolic upstroke and QRS component to 25% of systolic upstroke. This time measure of contraction is normalized by the ejection period (EP), as measured from onset of systolic upstroke, and defined as maximal rate of amplitude increase to the indication of dichrotic notch, as measured and defined as the maximal rate of amplitude decrease on the diastolic side; the derived strength of contraction similarly serving as variable ($dv/dt_{e,s}$) in Eq. 7, above.

Example 4

A primary measure for afterload is obtained by deriving the measure for contractility (as described in Example 1 or 2) from plethysmographic measurements at ear and finger sensing sites, and calculating the ratio of either normalized time periods or normalized amplitudes; the derived afterload serving as variable ($dv/dt_{e,s}$)/($dv/dt_{f,s}$) in Eq. 7, above.

Example 5

The determination and utility of a corrected pre-ejection period (PEP), which is described in detail in Co-pending U.S. application Ser. No. 12/011,122. In this example, PEP is used to determine cardiac stroke volume (SV) as the ratio of left ventricular ejection time, defined and measured as onset to dichrotic notch equivalent (as described above) to PEP. The derived value serves as variable (LVET/PEP) in Eq. 7, above.

Example 6

To estimate preload, a measure of ejected volume is obtained by measuring the time period in milliseconds between 90% of upstroke amplitude and 90% down stroke amplitude of the systolic maximum. The measured preload value is used in combination with the normalized slope (as determined per Examples 2 and 3).

A normal to high systolic upslope and a normal to high diastolic down slope combined with a longer than average time period between those two 90% points, is indicative of low ejection volume.

Example 7

There are several additional and readily identifiable (and useful) sections of the systolic upstroke of amplitudes of the plethysmograms that directly reflect a cardiac parameter. For example, the maximal rate of slope change and the maximal slope generally reflect contractility and afterload. The high-end slope from 90% from 100% of systolic maximum generally reflects preload, as well as weakened myocardium, when used in combination with PEP as delimiter.

Example 8

Referring to Equation 1, there is shown a mathematical relationship between a clinically important measure of cardiovascular performance (CP) and three cardiac function determinants (CFD), of which one is associated with preload, another with contractility and a third with afterload.

In this example, the cardiac performance comprises systolic blood pressure, $BP_{sys}$, which is determined (via Equation 1) by the mathematical relationship of three routinely determined clinical terms: (i) the wedge pressure via catheter for preload, (ii) the initial ventricular ejection velocity determined via Doppler ultrasound for contractility, and (iii) the pulse wave velocity, determined as the time difference between arrival at the left index finger of known distance from the aorta and the maximal deflection during the QRS signal of the ECG, as a measure of compliance and resistance for afterload. The mathematical function (f) is an empirically determined relationship between these measurable CFDs that provides the best fit to experimental data.

Example 9

In this example, the cardiac performance comprises diastolic blood pressure, $BP_{dia}$, which is determined (via Equation 1) by the mathematical relationship of three routinely determined clinical terms: (i) the central venous pressure integral during the right atrial filling period as determined by pressure sensing via catheter as a measure for preload, (ii) the time integral of deceleration of ventricular ejection velocity determined via Doppler ultrasound for contractility, and (iii) the time delay of the reflected wave determined as the difference to the systolic maximum in the plethysmogram from an arterial pressure sensor, for afterload. The mathematical function (f) is an empirically determined relationship between these measurable CFDs that provides the best fit to experimental data.

Example 10

In this example, the cardiac performance comprises systemic vascular resistance, which is determined (via Equation 1) by the mathematical relationship of three routinely determined clinical terms: (i) right atrial pressure in combination with pulmonary artery pressure integrals during the filling period as surrogates for left ventricular filling determined by pressure sensing via catheter as a measure for preload, (ii) pre-ejection period determined by valvular closing sound timing after max QRS and beginning of ejection in combination with maximal acceleration during the systolic upstroke period as determined by arterial pressure sensing, for contractility, and (iii) the difference in integrals of central and peripheral arterial blood pressure in the plethysmogram from arterial pressure sensors for afterload. The mathematical function (f) is an empirically determined relationship, by which the CFD for afterload is normalized for the variables preload and contractility, between these measurable CFDs that provide the best fit to experimental data.

Example 11

Referring back to Equation 2, above, there is shown a mathematical relationship between a clinically important measure of cardiovascular performance, stroke volume (SV), and three cardiac function determinants (CFD), of which one is associated with preload, another with contractility and a third with afterload.

In this example, SV is determined (via Equation 2) by the mathematical relationship of three routinely determined clinical terms, single use or combination: (i) central venous pressure, right atrial pressure, pulmonary artery pressure, lung fluid volume, width of ejection period in plethysmogram as a measure for preload, (ii) a combination of initial velocity and acceleration of ventricular ejection, pre-ejection period, muscle length shortening, time of pressure build-up and decay to diastolic preset value in plethysmogram for contractility, and (iii) pressure in large and small arteries, pulse wave velocity, time delay and width of the reflected wave sensor for afterload. The mathematical function (f) is an empirically determined relationship between these measurable CFDs that provides the best fit to the experimental data.

Example 12

Referring back to Equation 3, above, there is shown a mathematical relationship between the clinically important parameter of true contractility and residuals of afterload in the CFDs used for determining contractility.

In this example, the $CFD_1$ initial velocity of the systolic upstroke interval in the plethysmogram is contaminated by contributions of vascular compliance and resistance, which are subtracted via $CFD_2$ and $CFD_3$, the arrival time of the pressure wave at the peripheral location ear lobe and the time delay of the reflected wave peak. The mathematical coefficients a and b are empirically determined to provide the best fit to the experimental data.

Example 13

Referring back to Equation 4, above, there is shown a mathematical relationship between the clinically important parameter of true contractility and residuals of preload in the CFDs used for determining contractility.

In this example, $CFD_1$ the max acceleration during the systolic upstroke portion of the plethysmogram is contaminated by contributions of blood volume variability, which are subtracted in addition to the afterload contaminants $CFD_2$ and $CFD_3$, the arrival time of the pressure wave at the peripheral location ear lobe and the time delay of the reflected wave peak, as $CFD_4$ the width at half height of the systolic portion of the plethysmogram. The mathematical coefficients a, b and c are empirically determined to provide the best fit to the experimental data.

Example 14

In this example, the cardiac performance comprises diastolic blood pressure, $BP_{dia}$, which is determined (via Equation 1) by the mathematical relationship of three cardiac function determinants: (i) The cardiac function determinant associated with preload, i.e. $CFD_x$, is determined from the width measured in seconds of the ejection phase of the plethysmogram data; (ii) the cardiac function determinant associated with contractility, i.e. $CFD_y$, is determined at the inflection point from the normalized rate of change of the systolic upslope of the ejection phase and measured in 1/seconds; and (iii) the cardiac function determinant associated with afterload, i.e. $CFD_z$, is determined from the normalized rate of change of the systolic upslope at the inflection point and measured in 1/seconds also. The mathematical function (f) is an empirically determined relationship between these measurable CFDs that provides the best fit to experimental data.

Example 15

In this example, the cardiac performance comprises systolic blood pressure, $BP_{sys}$, which is determined (via Equation 1) by the mathematical relationship of three cardiac function determinants: (i) The cardiac function determinant associated with preload, i.e. $CFD_x$, is determined from the width measured in seconds of the ejection phase of the plethysmogram data; (ii) the cardiac function determinant associated with contractility, i.e. $CFD_y$, is determined as the maximal rate of increase from the normalized rate of change of the systolic upslope of the ejection phase and measured in 1/seconds; and (iii) the cardiac function determinant associated with afterload, i.e. $CFD_z$, is determined from the time difference of the peak systole and the max of the reflected wave. The mathematical function (f) is an empirically determined relationship between these measurable CFDs that provides the best fit to experimental data.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A method comprising:
   determining an estimate of a cardiac stroke index (SI) of a subject based on signals from
   a first plethysmograph adapted to be located on a first position of the subject, where said first position is on an ear of the subject,
   a second plethysmograph adapted to be located on a second position of the subject, where said second position is on a finger of the subject, and
   an electrocardiogram (ECG) sensor adapted to be located on the subject,
   where said determining is determined according to:
   $$SI=(14.02*LVET/PEP)*(1-0.3*((dV/dT_{e,s})/(dV/dT_{f,s})) *MAXIMUM(1.5,((dV/dT_{e,s})/(dV/dT_{e,d})))),$$
   where
   LVET=a time, in seconds, between onset of systole until a time post peak systole that a volume returns to less than 50% maximum,
   PEP is a pre-ejection period,
   $dV/dT_{e,s}$ is calculated using a systolic portion of a volumetric ear signal, normalized over a single pulse such that a minimum value=0 and a peak systole is 1 as $dV/dT_{e,s}$=MAXIMUM $(V_e(t)-V_e(t-0.05 \text{ seconds})/0.05$ seconds,
   $dV/dT_{f,s}$ is calculated using a systolic portion of a volumetric finger signal, normalized over a single pulse such that minimum value=0 and a peak systole=1 as $dV/dT_{f,s}$=MAXIMUM $(V_f(t)-V_f(t-0.05$ seconds$)/0.05$ seconds, and
   $dV/dT_{e,d}$ is calculated using a diastolic portion of a volumetric ear signal, normalized over a single pulse such that minimum value=0 and a peak systole=1 as $dV/dT_{e,d}$=MINIMUM $(V_e(t)-V_e(t-0.05$ seconds$)/0.05$ seconds.

2. A method comprising:
   determining an estimate of a cardiac stroke index (SI) of a subject based on signals from
   a first plethysmograph adapted to be located on a first position of the subject, where said first position is proximate a central circulation system of the subject,
   a second plethysmograph adapted to be located on a second position of the subject, where said second position is at a distal point on the body of the subject, and
   an electrocardiogram (ECG) sensor adapted to be located on the subject;
   where said determining is determined according to:
   $$SI=\alpha*LVET/PEP*(1-\beta*(((dv/dT_{e,s})/(dv/dT_{f,s}))*((dv/dT_{e,s})/(dv/dT_{e,d})))),$$ where
   LVET is a time, in seconds, between onset of systole until a time post peak systole that a volume returns to less than 50% maximum,
   PEP is a pre-ejection period,
   $dv/dT_{e,s}$ is a maximal systolic upslope of a signal from said first plethysmograph,
   $dv/dT_{f,s}$ is a the maximal systolic upslope of a signal from said second plethysmograph,
   $dv/dT_{e,d}$ is a maximal diastolic down slope of a signal from said first plethysmograph, and
   $\alpha$ and $\beta$ are constants determined by best fit of data to the equation
   $$SI=\alpha*LVET/PEP*(1-\beta*(((dv/dT_{e,s})/(dv/dT_{f,s}))*((dv/dT_{e,s})/(dv/dT_{e,d})))).$$

3. The method of claim 2, wherein said first position is on a nose, a forehead, an earlobe, a neck, an ear, an upper shoulder, or a chest of the subject.

4. The method of claim 2, wherein said second position is on a digit, a hand, an arm, a foot, a toe, or a leg of the subject.

* * * * *